(12) United States Patent
Cohen et al.

(10) Patent No.: US 11,872,386 B2
(45) Date of Patent: Jan. 16, 2024

(54) THIN FILM MASER EMITTER AND THIN PANEL PHASED ARRAY OF EMITTERS

(71) Applicant: Emad Eskandar, Swampscott, MA (US)

(72) Inventors: James Joseph Cohen, Wenham, MA (US); Emad N. Eskandar, Swampscott, MA (US)

(73) Assignee: Emad Eskandar, Swampscott, MA (US)

( * ) Notice: Subject to any disclaimer, the term of this patent is extended or adjusted under 35 U.S.C. 154(b) by 545 days.

(21) Appl. No.: 17/148,215

(22) Filed: Jan. 13, 2021

(65) Prior Publication Data
US 2021/0218213 A1   Jul. 15, 2021

Related U.S. Application Data

(60) Provisional application No. 62/961,263, filed on Jan. 15, 2020.

(51) Int. Cl.
*H01S 1/02* (2006.01)
*A61N 5/04* (2006.01)
(Continued)

(52) U.S. Cl.
CPC .......... *A61N 5/045* (2013.01); *A61B 18/1815* (2013.01); *A61B 90/36* (2016.02); *H01S 1/02* (2013.01); *H01S 1/06* (2013.01); *A61B 2018/0016* (2013.01); *A61B 2018/00446* (2013.01); *A61B 2018/00577* (2013.01); *A61B 2018/1861* (2013.01); *A61B 2090/374* (2016.02); *A61B 2090/3762* (2016.02); *A61N 2005/027* (2013.01)

(58) Field of Classification Search
CPC ......... H01S 1/02; H01S 3/1681; H01S 3/0933
See application file for complete search history.

(56) References Cited

U.S. PATENT DOCUMENTS

| 3,283,147 A | 11/1966 | Avakian |
| 4,949,347 A * | 8/1990 | Satoh ...................... C30B 33/00 423/446 |

(Continued)

FOREIGN PATENT DOCUMENTS

| CN | 109256656 A * | 1/2019 | ............... H01S 1/02 |
| WO | WO-2013175235 A1 * | 11/2013 | ........... G01R 33/343 |

(Continued)

OTHER PUBLICATIONS

International Search Report dated Apr. 7, 2021 in co-pending PCT application PCT/US2021/013261.

(Continued)

*Primary Examiner* — Joshua King
(74) *Attorney, Agent, or Firm* — Andrus Intellectual Property Law, LLP

(57) ABSTRACT

A MASER (Microwave Amplified Stimulated Emission of Radiation) emitter is fabricated of thin film components, including a thin film of nitrogen-implanted, epitaxial crystal diamond. The MASER elements can also include a controllable Q-switching layer and be arranged in a thin panel, phased array to generate a single beam of coherent, mode-locked, continuous wave MASER radiation.

20 Claims, 8 Drawing Sheets

(51) Int. Cl.
*A61B 90/00* (2016.01)
*A61B 18/18* (2006.01)
*H01S 1/06* (2006.01)
*A61B 18/00* (2006.01)
*A61N 5/02* (2006.01)

(56) References Cited

U.S. PATENT DOCUMENTS

| | | | |
|---|---|---|---|
| 9,042,413 B1* | 5/2015 | Brown | H01S 1/02 372/4 |
| 9,966,720 B2 | 5/2018 | Liu et al. | |
| 2003/0098979 A1 | 5/2003 | Dress et al. | |
| 2006/0262876 A1 | 11/2006 | LaDue | |
| 2009/0287274 A1 | 11/2009 | De Ridder | |
| 2012/0289763 A1 | 11/2012 | Boyden et al. | |
| 2013/0335706 A1 | 12/2013 | Schmitt-Manderbach et al. | |
| 2014/0072008 A1* | 3/2014 | Faraon | H01S 3/1681 372/45.01 |
| 2014/0326902 A1* | 11/2014 | Tahan | H01S 5/04 250/493.1 |
| 2015/0214687 A1* | 7/2015 | Oxborrow | H01S 1/02 372/4 |
| 2017/0077665 A1* | 3/2017 | Liu | H01S 1/005 |
| 2017/0367613 A1 | 12/2017 | Eckert et al. | |
| 2019/0117109 A1 | 4/2019 | Grundfest et al. | |
| 2019/0252842 A1 | 8/2019 | Breeze et al. | |

FOREIGN PATENT DOCUMENTS

| | | | | |
|---|---|---|---|---|
| WO | WO-2017015712 A1 * | 2/2017 | | A61B 5/0042 |
| WO | WO-2017015713 A1 * | 2/2017 | | G01K 11/00 |
| WO | WO-2018004549 A1 * | 1/2018 | | |
| WO | 2018026424 | 2/2018 | | |
| WO | WO-2018026424 A2 * | 2/2018 | | G01N 24/08 |
| WO | WO-2018051099 A1 * | 3/2018 | | B82Y 10/00 |
| WO | 2019021002 | 1/2019 | | |
| WO | WO-2019021002 A1 * | 1/2019 | | H01S 1/02 |
| WO | 2019202114 | 10/2019 | | |
| WO | 2019222436 | 11/2019 | | |

OTHER PUBLICATIONS

International Search Report dated Apr. 7, 2021 in co-pending PCT application PCT/US2021/013269.
International Search Report dated Apr. 6, 2021 in co-pending PCT application PCT/US2021/013279.
Anderson, et al. Observation of Bose-Einstein Condensation in a Dilute Atomic Vapor, Science, Jul. 14, 1995, New Series, vol. 269, No. 5221, pp. 198-201.
Asbell, et al. Conductive Keratopasty for the Correction of Hyperopia, TR Am Ophth Soc 2001; 99:79-87.
Bauch, Andreas Caesium atomic clocks: function, performance and applications, Meas. Sci. Technol. 14 1159.
Bond, et al. Interferometer techniques for gravitational-wave detection, Living Rev. Relativ (2016) 19:3.
Breeze, et al. Continuous-wave room-termperature diamond maser, Mar. 22, 2018, vol. 555, Nature, pp. 493-500.
Covey, et al. Illicit Dopamine Transients: Reconciling Actions of Abused Drugs Trends Neurosci. Apr. 2014.
Dirac, The Quantum Theory of the Emission and Absorption of Radiation, St. John's College, Cambridge and Institute for Theoretical Physics, Copenhagen, Feb. 2, 1927.
Einstein, A. The Quantum Theory of Radiation Mar. 1917.
Gordon, et al. The Maser-New Type of Microwave Amplifier, Frequency Standard, and Spectrometer, Physical Review, vol. 99, No. 4, Aug. 15, 1955.
Hernandez-Lopez, et al. D1 Receptor Activation Enhances Evoked Discharge in Neostriatal Medium Spiny Neurons by Modulating an L-Type Ca2+ Conductance, The Journal of Neuroscience, May 1, 1997 17(9):3334-3342.
Hoppe, et al. Laser interstitial thermotherapy (LiTT) in epilepsy surgery, British Epilepsy Association, Feb. 16, 2017.
Hubel, et al. Receptive Fields and Functional Architecture of Monkey Striate Cortex, J. Physiol. (1968) 195, pp. 215-243.
Mach, L. Via an interference refractory, Mar. 1892 (machine translation included).
Maiman, T.H. Stimulated Optical Radiation in Ruby, Nature Aug. 6, 1960 vol. 187 pp. 493-494.
Miloni et al. Laser Physics, Wiley & Sons, Inc. 2010.
Mountcastle, Vernon B. Modality and Topographic Properties of Single Neurons of Cat's Somatic Sensory Cortex, Department of Physiology, The Johns Hopkins University School of Medicine, Nov. 5, 1956.
Patel, et al. Studying task-related activity of individual neurons in the human brain, Nature Protocols, vol. 8 No. 5, 2013 pp. 949-957.
Reid, Macgregor S. Low-Noise Systems in the Deep Space Network, Jet Propulsion Laboratory, California Institute of Technology, Feb. 2008.
Reinstein, et al. Short term LASIK outcomes using the Technolas 217C excimer laser and Hansatome microkeratome in 46 708 eyes treated between 1998 and 2001, Br J Opthalmol 2012; 96:1173-1179.
Schawlow, et al. Infrared and Optical Masers, Physical Review, vol. 112, No. 6, Dec. 15, 1958 pp. 1940-1949.
Schultz, et al. Responses of Monkey Dopamine Neurons During Learning of Behavioral Reactions, Journal of Neurophysiology, vol. 67, No. 1, Jan. 1992 pp. 145-163.
Schultz, et al. Responses of Monkey Dopamine Neurons to Reward and Conditioned Stimuli during Successive Steps of Learning a Delayed Response Task, The Journal of Neuroscience, Mar. 1993, 13(3): 900-913.
Schultz, et al. Dopamine neurons report an error in the temporal prediction of reward during learning, Nature America Inc., Nature Neuroscience, vol. 1 No. 4, Aug. 1998 pp. 304-309.
Wu, et al. Modeling the Pulse Signal by Wave-Shape Function and Analyzing by Synchrosqueezing Transform, May 26, 2016.

* cited by examiner

THIN FILM MASER EMITTER AND THIN PANEL PHASED ARRAY OF EMITTERS

FIELD OF THE INVENTION

The invention relates to the Microwave Amplified Stimulated Emission of Radiation (MASER). More specifically, the invention pertains to thin film MASER emitters and the use of these devices in a phased array to generate a single beam of coherent MASER radiation. The phased array generates synthesized MASER radiation with a long coherence length.

BACKGROUND OF THE INVENTION

Microwaves are a form of Electromagnetic Radiation (EMR). Visible light is part of the electromagnetic spectrum, which ranges from radio waves to gamma rays. Electromagnetic radiation waves, as their names suggest, are fluctuations of electric and magnetic fields, which can transport energy from one location to another. Visible light is not inherently different from the other parts of the electromagnetic spectrum with the exception that the human eye can detect visible waves. Electromagnetic radiation can also be described in terms of a stream of photons which are massless particles each travelling with wavelike properties at the speed of light. A photon is the smallest quantity (quantum) of energy which can be transported. Electromagnetic radiation covers the range from radio waves to hard x-rays, which are also called gamma rays, see FIG. 1.

The interaction of electromagnetic radiation (EMR) and matter is central to current imaging techniques. EMR is conveyed by photons. The frequency of a photon is proportional to its energy in Equation 1:

$$E = h\nu = hc/\lambda \qquad \text{Eq. 1}$$

wherein E is energy, h is Planck's constant, $\nu$ is frequency, c is the speed of light, and $\lambda$ is the wavelength. Simply put, the higher frequency of the photon, the greater its energy.

Electromagnetic radiation interacts with matter through a limited number of mechanisms: transmission (including refraction and diffraction), reflection, absorption, or emission. Transmission implies that photons pass through a substance with minimal interaction, as is the case of visible light passing through a non-opaque gas. Refraction is a function of the different speeds with which electromagnetic radiation is transmitted through different substances, whereas diffraction describes its behavior as it passes through narrow apertures or around edges. Reflection describes the circumstance where an incident beam of electromagnetic radiation encounters a reflective surface such that the resultant beam has an angle equal to the incident beam. Absorption refers to a specific interaction between a photon and an atom or a molecule and emission refers to the discharge of a photon from an atom or a molecule.

At one end of the EMR spectrum are X-rays representing high-energy and high-frequency photons. Interaction of such a photon with an atom is associated with considerable energy transfer. If a photon in the x-ray band of the spectrum interacts with an atom, it causes an electron to be completely ejected from its shell, ionizing the host atom, disrupting its covalent bonds, and potentially damaging or breaking molecules including strands of DNA. At the opposite end of the spectrum are radio-waves, which are composed of low-energy, low-frequency photons. Photons in the radio-wave region of the spectrum generally have weak interactions with biological molecules and are transmitted through without change to either the photon or the molecules (FIG. 1).

Photons in visible light interact with biological molecules primarily through absorption and reflection. Visible light does not transmit through the body, meaning that photons are either reflected or absorbed. Reflected photons give rise to the color of biological tissues, whereas absorbed photons add kinetic energy, or heat, to animal tissues. Microwave emissions occupy a portion of spectrum between visible light and radio-waves and have properties of both. Depending on the frequency, microwaves can interact with biological molecules through, absorption and emission (as with visible light) or be transmitted (as with radio-waves).

Quantum physics describes the behavior of atoms and electrons in relation to discrete quanta or packets of energy. Table 1 below provides the definition of common terms used in the field of quantum physics:

TABLE 1

| Term | Definition |
| --- | --- |
| Ground State | An atom with its electrons at their lowest orbital is said to be in its Ground State |
| Excited State | An atom is in a higher energy state than its ground state reflecting electrons being in higher orbitals |
| Spontaneous Absorption | Electron transitions from lower energy to higher energy orbital by absorbing a photon or heat |
| Spontaneous Emission | Electron transitions from higher energy to a lower energy orbital by emitting a photon |
| Stimulated Emission | Electron is stimulated by photon to transition from higher to lower energy by emitting another photon |
| Coherence | Photons have the same frequency and phase in stimulated emission |

Electrons can absorb or release energy in the form of photons or heat. However, electrons are constrained to occupy discrete orbitals at specific energy levels. Electrons can transition from a lower orbital to higher orbitals through absorbing a photon with a frequency equal to the difference in energy between two orbitals in a process called spontaneous absorption. Excited electrons relax back to their preferred lower energy levels by emitting photons having a frequency equal to the difference in energy between two orbitals through the process of spontaneous emission (Dirac & Bohr, 1927). Excitation into higher energy states can be only induced by photons with the requisite frequency. Similarly, relaxation emits photons with the specific frequency corresponding to a particular transition.

The state of an electron can be described by four quantum numbers—the principal quantum number or orbital n (orbital), the azimuthal quantum number $\ell$ (subshell), the magnetic quantum number m $\ell$ (magnetic moment) and the spin quantum number $m_s$. The energy of an electron is determined by its orbital and subshell. The Pauli exclusion principle states that no two electrons in an atom can have the same values for all four quantum numbers, though it is possible for electrons to have different quantum numbers but have the same energy levels, which are called degenerate orbitals. Electrons can become excited and transiently occupy higher energy orbitals through the absorption of photons or heat. Relaxation of electrons can occur through radiative decay with the emission of photons, or through non-radiative decay with the emission of heat.

At the level of atoms, spontaneous absorption can occur with photons frequencies in the ultraviolet, visible, and infra-red range of the spectrum. Electron relaxation may occur through a series of smaller steps associated with emission of photons with lower energy and frequency including those in the micro-wave range. The energy of an atom is also a quantum state and reflects the quantum states, as defined by the four quantum numbers, of all its constituent electrons. Molecules have additional degrees of freedom, beyond the four quantum numbers, that are described as molecular vibration and rotation. Transitions between these states are also quantal and generally occur through the absorption and emission of photons with frequencies in the infra-red or microwave range.

Transitions between different quantum energy states can be represented using Jablonski diagrams. An atom or molecule in the lowest energy state possible, known as the ground state ($E_0$), can absorb a photon with a specific frequency whereby it becomes excited and attains a higher energy state ($E_1$) FIG. 2A. A substance made of such atoms will absorb this characteristic frequency, and likely other specific frequencies, thereby imparting its color. The atom or molecule tends not to stay in this excited state and relaxes back to its ground state in several ways. In FIG. 2A, the atom or molecule relaxes in two quantum steps, through an intermediate quantum state, and emits two photons both of which have lower frequency and energy than the absorbed photon. The photons emitted will be characteristic for the energy transitions appropriate for that particular atom or molecule, and by studying the light emission the matter under investigation can be determined.

In FIG. 2B, the excited atom or molecule initially loses energy not by emitting a photon but by a non-radiative process (heat) emission, to reach an intermediate state. The atom or molecule then relaxes from the intermediate energy state to the ground state by the emission of a lower energy photon than originally absorbed. A uniform collection of atoms or molecules can relax through a combination of mechanisms, the distribution of which, depends on the lifetime of the different intermediate states and external factors such as magnetic fields.

The fundamental idea behind the process called stimulated emission was first described in 1917 as part of a more extensive paper by Albert Einstein on "The Quantum Theory of Radiation" (Einstein, 1917). In stimulated emission, an excited electron is stimulated by an incident photon, not into a higher orbital but rather into a lower orbital (FIG. 3). In this case, the incident photon is not absorbed, but rather induces the excited electron back into its preferred lower-energy ground or state. This downward transition of the electron results in the emission of a photon. Initially, there are two quanta—the excited electron and the incident photon. Subsequently, there are also two quanta—the incident photon and the emitted photon. Hence, energy is conserved. Critically, however, after the encounter both the incident photon and the emitted photon, having been transiently enmeshed, emerge having the same phase and frequency. Thus, there are three important features to this process. 1) Before emission, the incident photon has a frequency equal to the difference in energy between the excited state and the lower energy state. 2) After emission, both the incident and emitted photon are coherent, having the same frequency, phase, and direction. 3) The process starts with one photon having the requisite frequency to generate an emission and ends with two photons having the necessary frequency to evoke an emission. These two coherent photons can stimulate other atoms potentially leading to 4 coherent photons, which could lead to 8 coherent photons etc.

Hence, under the right circumstances and with a source of energy, this can be a self-reinforcing or multiplicative process. Upon reaching a tipping point (i.e. the lasing or masing threshold) this process creates a surfeit of coherent photons having the same frequency (color in the case of lasers), phase, and direction—a LASER beam for visible light or—a MASER beam—for microwaves. Such beams have unique properties and applications that cannot be realized with incoherent light or microwave radiation, which has a mixture of frequencies, phases, and directions.

In 1955, American physicist Charles Townes of Columbia University, an expert in molecular spectroscopy, and his co-workers, showed how stimulated emission could be used to make a device for generating coherent microwave emissions, which they called a MASER (i.e., Microwave Amplified Stimulated Emission of Radiation) (Gordon et al., 1955). Three years later, Townes and Arthur Schwalow explained how to extend the idea to visible and infrared frequencies and make an "Optical MASER", a name later changed to LASER (Schawlow & Townes, 1958). Their ideas were subsequently realized with the demonstration of a functional Laser by Theodore Maiman at Hughes Research Laboratories in 1960 (Maiman, 1960). Since then, there has been an increase in sophistication surrounding the design, fabrication, and use of coherent emissions in the visible region of the EMR spectrum.

There are many important steps in the practical implementation of a successful system. The first is to identify a substance having favorable quantum transitions, either on theoretical or empirical grounds. This substance is called the gain medium. Identification and selection of the gain medium entails several considerations: 1) The substance must have suitable transition states that can be stimulated at the desired frequency. 2) Useful transitions are commonly associated with frequencies in the visible, infra-red or microwave range. 3) The sequence of transitions can be complex, and a limited number of substances maybe be-suitable for stimulated emission. 4) Favorable substances may relax through different sequences of state transitions including a ground state, an excited state, and a metastable excited state that on-average takes longer to relax back to the ground state than competing states.

Once a suitable gain medium is identified, the next practical step is to establish the process of stimulated emission by providing the energy necessary to establish and drive the process. This energy is usually provided in the form of photons, a process called photon-pumping. Photons can be provided by a laser, a light-emitting diode (LED), or other means. The next step is to create conditions that preferentially enrich the metastable state so that stimulated emissions overtake spontaneous emissions as the predominant process. This may involve using electrical fields, magnetic fields, or a means for promoting resonance in the desired frequency using a resonator box (LASER systems have mirrors while MASER systems typically have a physical cavity). Finally, it is important to consider whether the system should be designed to have a lower but constant output (Continuous Wave) or higher but periodic output (Pulsed Wave) (Wu et al., 2019).

Continuous-wave lasers produce a continuous, uninterrupted beam of light, ideally with a very stable output power. The exact wavelength(s) or line(s) at which this occurs is determined by the characteristics of the laser. For example, $CO_2$ molecules readily lase at 10.6μm, while neodymium-based crystals (like YAG or vanadate) produce wavelengths in the range between 1047 and 1064 nm. Each laser wavelength is associated with a linewidth, which depends on the gain bandwidth of the lasing medium and the design of the optical resonator. The ideal laser would produce only one wavelength, however, even a single laser line actually covers a range of wavelengths. For example, laser diodes produce light over a wavelength range of several nanometers corresponding to their "gain bandwidth." The specific wavelengths of the output beam within this gain bandwidth are determined by the longitudinal modes of the resonant cavity, and the actual output wavelengths of the laser will correspond to longitudinal cavity modes that fall within the gain bandwidth.

Pulsed laser devices produce trains of very brief emissions lasting 0.5 to 500 ns. The most important characteristic of a nanosecond-pulsed laser is the capability to "store" and release energy very rapidly, on a nanosecond scale, so that the laser output can achieve kilowatts to megawatts of peak power. Materials such as excited dimers (or "excimers") of a noble gas with a halogen, such as Ar:F and Xe:Cl, sustain laser action for only several nanoseconds and can only be used for pulsed operation. Some lasers, like Nd or Yb diode-pumped solid-state (DPSS) lasers, can be used in either CW or pulsed operation, while other lasers are not suitable for any pulsed operations. The key to producing these energetic pulses is storing energy from the pump in the atoms or molecules of the lasing medium by preventing the laser gain and the amplification process. Then, when the stored energy is at its maximum, lasing action is rapidly enabled.

A Q-switch is essentially a means of spoiling or disrupting the light path within the resonator, with a very fast response time. Q is shorthand for quality, in this case, quality of the cavity or of light transmission. Hence in one state (low Q) the switch creates cavity loss, poor quality of resonance, and prevents lasing; in the other case (high Q), there is essentially no loss, so lasing can occur. The most used Q-switch devices for lasers are electro-optic (EO) and acousto-optic (AO) modulators. In $E_O$ modulators, a crystal rotates the polarization of light passing through it when a voltage is applied and disrupts lasing. In an AO modulator, a crystal deflects the intracavity beam by a fixed angle when radio frequency (RF) power is applied, also disrupting lasing.

Laser materials with a wide gain-bandwidth, such as Ti:Sapphire, can produce a broadband frequency output (tens of nanometers of more). Detailed examination reveals that this output consists of hundreds, thousands, or even tens of thousands of individual longitudinal modes. These modes gain and lose intensity and have random phase relationships relative to each other. In mode-locking, the relative phase of all these modes is fixed. There are two categories of mode-locking called active and passive mode-locking. Active mode-locking entails fast gating of the cavity (for example, by using an AO modulator as in the Q-switching). Passive mode-locking is performed through materials that change their properties in response to the generation of mode-locked emission. One technique uses a "bleachable" optic, which is essentially a special mirror within the cavity that approaches 100% reflectivity when its absorbing semiconductor layer is overloaded by the high peak power of mode-locked operation.

Until recently, solid-state MASERs have been large devices with low efficiency and considerable heat generation, necessitating cryogenic cooling to sustain continuous wave operation. Hence, their utility was limited to certain applications. Hydrogen MASERs have been used as atomic frequency standards (Bauch, 2007). In other applications, the Jet Propulsion Laboratory developed a MASER to provide amplification of microwave signals from deep space probes (Reid, 2008).

In 2018, a room temperature, continuous wave MASER was achieved using synthetic diamonds containing specifically engineered lattice defects (Breeze et al., 2018). A laser was used to pump photons into nitrogen-vacancy defects within the diamond matrix. Breeze et al. describes an experimental benchtop MASER system that is essentially a single emitter housed in a large copper resonator box, which is not a design suitable for commercial manufacture nor for use in large panel arrays.

On May 8, 2018 Renbao Liu, and Liang Jin from the Chinese University of Hong Kong, were issued U.S. Pat. No. 9,966,720. This patent describes a system and a method for coherent emission of continuous wave MASER beams from a bulk diamond crystal gain medium having nitrogen vacancy centers. The system uses optical pump energy within a moderate magnetic field. The patent indicates that the MASER or amplifier functions at room temperature (15*C-50*C) in the continuous-wave mode. The gain medium is bulk diamond single crystal, with the emitters nitrogen-vacancy (NV) centers in the diamond.

Synthetic-Aperture Imaging (SAI) is a form of imaging that is used to create two-dimensional images or three-dimensional reconstructions of objects. SAI uses the motion or the dimensional displacement of the detector over a target region to provide finer spatial resolution than conventional array or detector scanning. SAI detectors are typically mounted on a moving platform, such as an aircraft or spacecraft. The technology has its origins in an advanced form of side looking airborne radar (SLAR). The distance the SAI device is displaced or travels over a target in the time taken for the radar pulses to return to the antenna creates the large synthetic aperture (the size of the detector). Typically, the larger the aperture, the higher the image resolution will be, regardless of whether the aperture is physical (a large detector) or synthetic (a moving detector array)—this allows SAI to create high-resolution images with comparatively small physical or 2-dimensional detector arrays. Additionally, SAI has the property of having larger apertures for more distant objects, allowing consistent spatial resolution over a range of viewing distances.

To create an SAI image, successive pulse trains are transmitted to "illuminate" a target, and the convolved mixed interferometric beam is received and recorded. The beams are transmitted and the convolved beams are received using single beam-forming mixers. As the SAI device is scanned, the detector relative to the target changes with time. Signal processing of the successive recorded pulse trains allows the combining of the recordings from these multiple detector positions. This process forms the synthetic antenna aperture and allows the creation of higher-resolution images than would otherwise be possible with a given 2-dimensional static array. SAI is capable of high-resolution remote sensing, as SAI can select frequencies to avoid signal attenuation. SAI has continuous imaging capability as illumination is provided by the synthetic aperture emitter.

Synthetic aperture images have wide application in remote sensing and mapping. Applications of SAI include topography, oceanography, glaciology, geology (for example, terrain discrimination and subsurface imaging), and forestry, including forest height, biomass, deforestation. Volcano and earthquake monitoring use differential interferometry to detect subtle changes in elevation. SAI can also be applied for monitoring civil infrastructure stability such as bridges. SAI is useful in environment monitoring such as oil spills, flooding, urban growth, global change and military surveillance, including strategic policy and tactical assessment. SAI can be implemented as inverse SAI by observing a changing or moving target over a substantial time with a stationary antenna.

A synthetic-aperture detector is an imaging system mounted on a moving platform, or on a 3-D detector array accessible in a temporally regular fashion. Electromagnetic waves are transmitted sequentially, the modulated beam scatters or echoes and is collected, and the system stores the data for subsequent processing. As transmission and reception occur at different times, they map to different positions. The well-ordered combination of the received signals builds a virtual aperture that is much larger than the physical detector array. That is the source of the term "synthetic aperture," giving it the property of an imaging system. The range direction is parallel to the 3-dimensional offset and perpendicular to the azimuth direction.

Basic principle: The 3D processing is done in two stages. The azimuth and range direction are focused for the generation of 2D (azimuth-range) high-resolution images, after which a digital elevation model (DEM) is used to measure the phase differences between complex images, which is determined from different look angles to recover the height information. This height information, along with the azimuth-range coordinates provided by 2-D synthetic aperture focusing, gives the third dimension, which is the elevation. The first step requires only standard processing algorithms. The second step requires additional pre-processing such as image co-registration and phase calibration. In addition, multiple baselines can be used to extend 3D imaging to the time dimension. 4D and multi-D SAR imaging allows imaging of complex scenarios and has improved performance with respect to classical interferometric techniques such as persistent scatter interferometry.

The SAI algorithm, as now described, generally applies to phased arrays. A three-dimensional array (a volume) of scene elements is defined, which represents the volume of space within which targets exist. Each element of the array is a cubical voxel representing the probability (or "density") of a scattering surface being at that location in space. Initially, the SAI algorithm gives each voxel a density of zero. Then for each captured waveform, the entire volume is iterated. For a given waveform and voxel, the distance from the position represented by that voxel to the detector(s) used to capture that waveform is calculated. That distance is represented as time delay of the waveform. The sample value at that position in the waveform is then added to the voxel's density value. This represents a possible signal from a target at that position. Note there are several optional approaches here, depending on the precision of the waveform timing, among other things. For example, if phase cannot be accurately determined, only the envelope magnitude (with the help of a Hilbert transform) of the waveform sample might be added to the voxel. If waveform polarization and phase are known and are sufficiently accurate, then these values might be added to a more complex voxel that holds such measurements separately.

After all waveforms have been iterated over all voxels, the basic SAI processing is complete. What remains, in the simplest approach, is to decide what voxel density value represents a solid object. Voxels whose density is below that threshold are ignored. Note that the threshold level must be higher than the peak energy of any single wave, otherwise that wave peak would appear as a sphere (or ellipse, in the case of multi-static operation) of false "density" across the entire volume. Thus to detect a point on a target, there must be at least two different antenna echoes from that point. Consequently, there is a need for large numbers of detectors positions to properly characterize a target. The voxels that passed the threshold criteria are visualized in 2D or 3D.

Optionally, added visual quality can sometimes be had by use of a surface detection algorithm like marching cubes.

Synthetic Aperture via Phased Array Control: Provided that the wave propagating emitter is stable and controllable, the well-established principles of phased array beamforming may be utilized to synthesize a diffraction limited MASER beam with a determinate numerical aperture. Since the MASER emitters emit diffraction limited energy isotropically, it is necessary to synthetically create a wave front that has selective directionality and mode locked character adequate for the contemplated pass length. The principles underlying wave addition may be applied.

Shifted emission phased array principles have been widely used in radar, sonar, seismology, oceanology, and medical imaging. Simply stated, a "phased array" is a group of emitters or sensors located at distinct spatial locations in which the relative phases of the signals are varied in such a way that the overall gestalt propagation mode is reinforced in a selectable direction and deconstructed in all other directions. The phased array principles have allowed the development of emitter and detector assemblies that can beamform and beam steer without any mechanical control.

Phased arrays can act as both wave transmitters (emitters) and wave receivers (detectors). When a phased array works in transmission mode, the relative amplitude of the signals radiated by the array in different directions determines the effective radiation pattern of the array. In practice, a phased array may be used to point toward a fixed direction, or to scan rapidly in azimuth or elevation. The array acts as a spatial filter, attenuating all signals except those propagating in certain directions. "Beamforming" is the name given to a wide variety of array-processing algorithms that are used to focus the signal-receiving or signal-transmitting abilities of the array in a particular direction. A beam refers to the main lobe of the directivity pattern. Beamforming can apply to transmission from the array, to reception in the array, or to both. A beamforming algorithm points the array's spatial filter toward desired directions. This is similar to the dish antenna of conventional radar swiveling to steer its beam into a desired direction; however, the phased-array beam-steering is achieved algorithmically rather than physically. The beamforming algorithm generally performs the same operations on the sensors' signals regardless of the number of sources or the character of the noise present in the wave field.

A phased array system whether requires fine frequency and phase coherence to a specific and stable operating mode. That may be achieved by a variety of means or by the use of a coherent emitter such as a maser. Symbolically all phased arrays of any integer plurality of emitters (N) is an example of N-slit diffraction provided that the EMR field at the detection point is a consequence of the coherent addition of N point sources in a line.

Since each emitter behaves as a slit diffractor or a point isotropic radiator the diffraction pattern can be derived by summing the phase shift y to the fringing term. Starting with N-slit diffraction pattern with N slits of equal size and spacing d $$\psi = \psi_0 \frac{\sin\left(\frac{\pi a}{\lambda}\sin\theta\right)}{\frac{\pi a}{\lambda}\sin\theta} \frac{\sin\left(\frac{N}{2}kd\sin\theta\right)}{\sin\left(\frac{kd}{2}\sin\theta\right)}$$

Fringe effects must be included: therefore, it is necessary to add the y term to the kd sin θ to produce:

$$\psi = \psi_0 \frac{\sin\left(\frac{\pi\alpha}{\lambda}\sin\theta\right)}{\frac{\pi\alpha}{\lambda}\sin\theta} \frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}$$

The intensity of the wave is calculated by taking the square of the wave function.

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}\right)^2$$

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{\pi}{\lambda}Nd\sin\theta + \frac{N}{2}\phi\right)}{\sin\left(\frac{\pi d}{\lambda}\sin\theta + \frac{\phi}{2}\right)}\right)^2$$

For convenience it assumed that the emitters are separated by $$d = \frac{\lambda}{4}$$

apart (any scalar fraction of the wavelength would function as well).

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{\pi}{4}N\sin\theta + \frac{N}{2}\phi\right)}{\sin\left(\frac{\pi}{4}\sin\theta + \frac{\phi}{2}\right)}\right)^2$$

Sine achieves its maximum value at $$\frac{\pi}{2},$$

thus, the numerator or the second term=1.

$$\frac{\pi}{4}N\sin\theta + \frac{N}{2}\phi = \frac{\pi}{2}$$
$$\sin\theta = \left(\frac{\pi}{2} - \frac{N}{2}\phi\right)\frac{4}{N\pi}$$
$$\sin\theta = \frac{2}{N} - \frac{2\phi}{\pi}$$

As N gets large, the result will be overshadowed by the $$\frac{2\phi}{\pi}$$

term. In a oscillatory system, it is expected that sine will oscillate between −1 and 1, therefore setting $$\phi = -\frac{\pi}{2}$$

will provide the maximum energy on an angle derived by $$\phi = \sin^{-1} 1 = \frac{\pi}{2} = 9°$$

If an adjustment to the angle at which the maximum energy is emitted is require, it is only necessary to adjust the phase shift φ between successive emitters.

This technique can control any amount of paired integer elements in a phased array emission device. It is through this means that a nascent isotropic room temperature MASER oscillator can have a plurality of similar devices organized and controlled to produce a coherent beam of extremely large and stable characteristics. Inversely, a similarly active detector array will be able to deconstruct such a beam in order to get information that would otherwise be lost in the diffraction blur.

One object of the present invention is to develop a commercially viable MASER emitter having a thin film gain medium, e.g. a thin film of nitrogen implanted diamond, that operates at room temperature. Another object of the invention is to develop a controllable phased array of MASER emitters, which enables the output of a single mode-locked coherent MASER beam.

Controlled MASER radiation, having different characteristics from LASER radiation, provides the potential to penetrate many objects, including biological objects, for purposes of imaging, diagnostics, or enervation, that are not possible with LASER radiation. It is contemplated that controlled, continuous wave MASER radiation at low energy levels can be used effectively in many of these applications. For example, in medical applications, it is contemplated that the energy level can be controlled so that the dose of radiation for a patient would be negligible and harmless.

SUMMARY OF THE INVENTION

In one aspect, the invention is directed to a MASER emitter capable of outputting coherent microwave energy in which the gain medium comprises an active epitaxial layer, namely a thin film layer of nitrogen-implanted, epitaxial crystal diamond. In contrast to a gain medium of nitrogen-doped bulk diamond, this invention involves the use of an epitaxially grown diamond layer in which nitrogen is then implanted. The inventor has shown that continuous wave, coherent MASER emission can be achieved using a nitrogen-implanted, epitaxial diamond layer as the gain medium. Such epitaxial films are capable of being fabricated in a reliably consistent manner, and contemporaneously across a large number emitters in an array. Accordingly, thin film and/or epitaxial fabrication techniques can be used to build the necessary layers of the MASER emitter and can be implemented on a large scale to fabricate panel arrays of MASER emitters.

Bulk materials can be synthesized by various techniques. For example, the Bridgman-Czochralski technique starts with a "germ" (or precursor) of the material which undergoes a thermodynamic cycle that leads to the formation of a cylindrical crystal with typical dimensions of a few centimeters exhibiting overall the properties of the initial germ.

The growth technique used to grow a bulk crystal strongly influences the properties of the final material.

Epitaxy defines a category of crystal growth techniques for material deposition, in which new crystalline layers (called epitaxial layers) are formed, one on top of the other, with one or more well-defined orientations with respect to the crystalline substrate. Epitaxial growth usually starts with the formation of islands on the substrate, which connect forming a "wetting layer" that drives the growth of the epitaxial layer. The growth then proceeds layer by layer, in a very controlled way. Epitaxial layers grow on top of a substrate of the same material or on different materials. When the substrate is a different material, a critical issue is the matching of the lattice parameter of the substrate and the epitaxial layer, which may require the use of buffer layers to compensate for the misfit stress. When the substrate is the same material the most critical point is the relative orientation of substrate and epilayer. In the example discussed herein, the epitaxial diamond layer is formed in the (1,1,1) orientation.

The nitrogen-doped bulk diamond requires a thermal annealing process to activate the nitrogen vacancies. Thermal annealing cannot be used when forming the gain medium on layers of other components. Accordingly, in accordance with one aspect of the invention, nitrogen is implanted in the epitaxial diamond and activated without thermal annealing so that the gain medium can be formed on other layers.

The nitrogen implantation step can be accomplished by bombarding the epitaxial film with nitrogen under the appropriate conditions. In the exemplary embodiment of the invention, the crystal diamond film has a thickness of about 10 id. For commercial applications of the invention, the thickness of the epitaxial layer of gain medium should be chosen to properly balance thermal and mechanical robustness with the capability of growing the epitaxial layer without defects. A suitable thickness of the gain medium in commercial applications is in the range between 5µ so to no more than about 30 to 40 id. In the exemplary embodiment of the invention using nitrogen-implanted epitaxial diamond, the relevant metastable state in the nitrogen-vacancy (NV) centers has a lifetime of ~1.6 microseconds, which is sufficient for generating continuous wave coherent MASER emissions, but unlikely to generate transients or other undesirable effects. Exposure of the nitrogen-implanted, epitaxial diamond layer to beams of swift heavy ions and low-energy electron radiation has been shown to useful to active the nitrogen-vacancy centers.

An LED outputs light to pump photons into the active epitaxial layer at a level sufficient to cause coherent microwave emission. In the exemplary embodiment, the LED outputs light at 530 nm.

The active epitaxial film as mentioned is the gain medium for the MASER and is located between a first resonator layer and a second resonator layer. In exemplary embodiments, the resonator layers are dielectric materials that are transparent to microwaves but together form a resonance chamber for the MASER. In the exemplary embodiment, the dielectric material are thin-film polymers layers made of polystyrene, which are effective for forming a dielectric reflector for microwaves at the wavelength emitted by the MASER. Other materials may be used for the resonator layers.

A MASER constructed in accordance with the invention can operate at room temperature. In order to maintain an appropriate temperature for the MASER device, a thermoelectric Peltier slab can be located adjacent the LED layer.

In another aspect of the invention, the MASER emitter is constructed with a controllable, active Q-switch between the first resonator layer and the gain medium. For example, in the exemplary embodiment of the invention, the Q-switch is a CCD-controlled layer of nematic molecules. An exemplary material for the Q-switch layer is Strontium Zinc Chloride.

In another aspect, the invention is directed to a phased-emitter array comprising a plurality of MASER emitters as described above in a thin panel arrangement. MASER emitters are arranged in a two-dimensional plane, and desirably other MASER emitters are arranged in a plane offset orthogonally to the first plane of emitters. Each emitter is capable of emitting coherent microwaves, and the Q-switches are controlled so that the phased array as a whole forms a single beam of coherent, mode-locked MASER radiation. In this preferred embodiment, the frequency and phase of the MASER radiation are tunable. For example, once masing begins, the Q-switches can be controlled to adjust phase and frequency of the beam, and can be controlled to include two or more characteristic frequencies of the beam, e.g. a coupling component and a modulation component of the beam. The offset provides spatial discrimination and provides greater flexibility to the control of the Q-switches. The number of individual emitters in the array depends on the application but is expected to be on the magnitude of $10^2$ to $10^6$ depending on the given application. Also, desirably, the distribution of energy in the coherent MASER radiation is orthogonally Gaussian. Gaussian orthogonality is achieved by adjusting the LED pump energy and coordinating the operation of the Q-switches. The orthogonally Gaussian beam can be passed through a collimator and an aperture to block the low energy fringe (e.g. less than 1/E 2) to create a clean coherent beam.

Accordingly, the invention provides the capability of fabricating a MASER emitter that operates at or near room temperature and can be implemented in a thin panel array capable of outputting continuous coherent, mode-locked MASER radiation with Gaussian orthogonality. The phased array generates synthesized MASER radiation with a long coherence length. Such an output may be advantageous for many technical applications, for example use in biomedical imaging of biological objects like the human brain, or in therapeutic procedures targeting pathogenic molecules with a signature frequency. The energy level of the MASER radiation can be made relatively low, so that it does not affect the patient other than for its intended purpose.

DETAILED DESCRIPTION

In 2018, Breeze et al., successfully demonstrated a room-temperature MASER operating in continuous wave mode (Breeze at, 2018). The most critical factor in their success was the use of a nitrogen-doped, bulk diamond. The device used a laser to pump photons into the nitrogen-doped, bulk diamond, which was housed in a copper resonator cavity. At 0.4 W of optical power, the masing threshold was reached. The device generated MASER emission in continuous wave mode, and was stable for all experiments, the longest being more than 10 hours.

Figure 4:
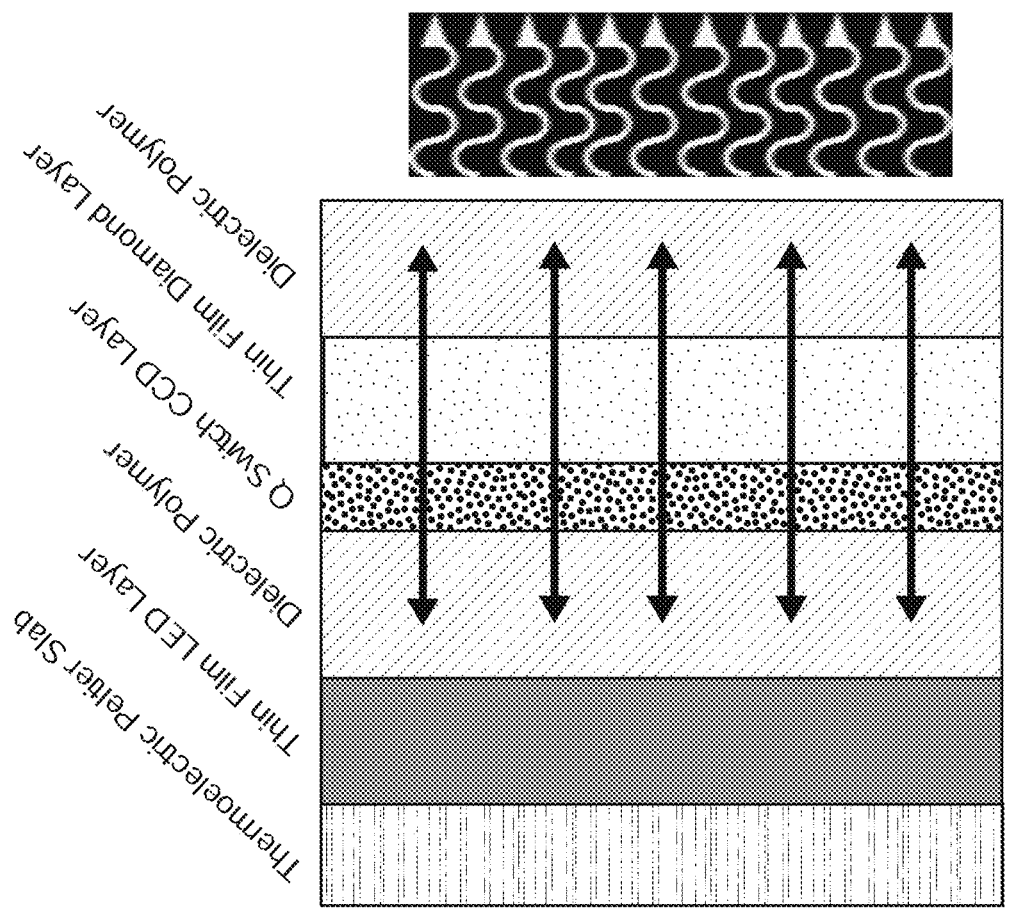
FIG. 4 is an illustration showing a MASER element constructed in accordance with an exemplary embodiment of the invention.

In contrast to the Breeze et al. device, the present invention uses layers of thin film to fabricate MASER emitters, and phased arrays of MASER emitters. FIG. 4 illustrates the layer components of a single MASER emitter 10 constructed in accordance with an exemplary embodiment of the invention. The gain medium 12 is a nitrogen-implanted layer of epitaxial crystal diamond, e.g., about 10μ in thickness. The layered components 12, 14, 16, 18, 20, and 22 are layered for example on a standard printed circuit board substrate. A thermo-electric Peltier slab 22 is the base layer and is adjacent the thin film, high-output LED (Light Emitting Diode) layer 18. The LED layer is desirably made of an alloy of Ga, Al, and In as cations, and N as the anion and is controlled to receive the required forward voltage to generate light waves at 530 nm. The current level is adjusted to control the lumens of light output from the LED and ensure that the masing threshold is reached. The Peltier slab 22 is controlled to reduce heat build-up in the LED layer 18 and otherwise ensures that the temperature of the LED 18 is within the range for suitable effectiveness. The thin film, high-output LED layer is the photon pump for the MASER emitter 10.

Alternating layers of dielectric polymers 14, 16 are made of materials chosen to reflect microwaves 24 emitted in the active layer 12 (i.e. the gain medium) and provide the sides of the resonator cavity for masing in the active layer 12. MASER wavelengths are orders of magnitude greater than the dimensions of a single emitter 10. The alternative approach would be to house the entire thin panel array in a physical resonant cavity. This would severely limit its practical application, and being a rigid physical structure, also limit the potential for tunability. In FIG. 4, reference number 24 refers to the microwaves being generated by the gain medium 12 and reflected by the layers of dielectric material 14, 16. Reference number 26 refers to the continuous emission of coherent microwave emission once the masing threshold is met.

A layer of Q-switching material 20 made of nematic molecules deposited onto the active layer 12. The Q-switching material 20 is capable of being CCD (charge coupled device) controlled and provides an interface for addressable control of the emission and entrainment of coherent emissions across a phased array of emitters 10. Accordingly, in accordance with another aspect of the invention, a phased array 28 (FIG. 5) of thin panel MASER emitters is controlled to output a single beam of mode-locked, coherent MASER radiation.

Still referring to FIG. 4, the layers of the emitter 10 are desirably formed on a substrate using lithographic and/or thin-film epitaxial techniques. The thickness of the layers in the exemplary embodiment is 50 nm~120 nm and ~220 nm.

Figure 5:
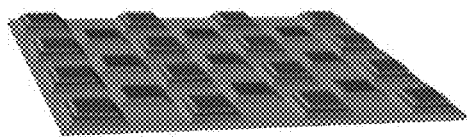
FIG. 5 is a diagram showing a thin panel, phased-emitter array constructed in accordance with an exemplary embodiment of the invention.
Figure 6:
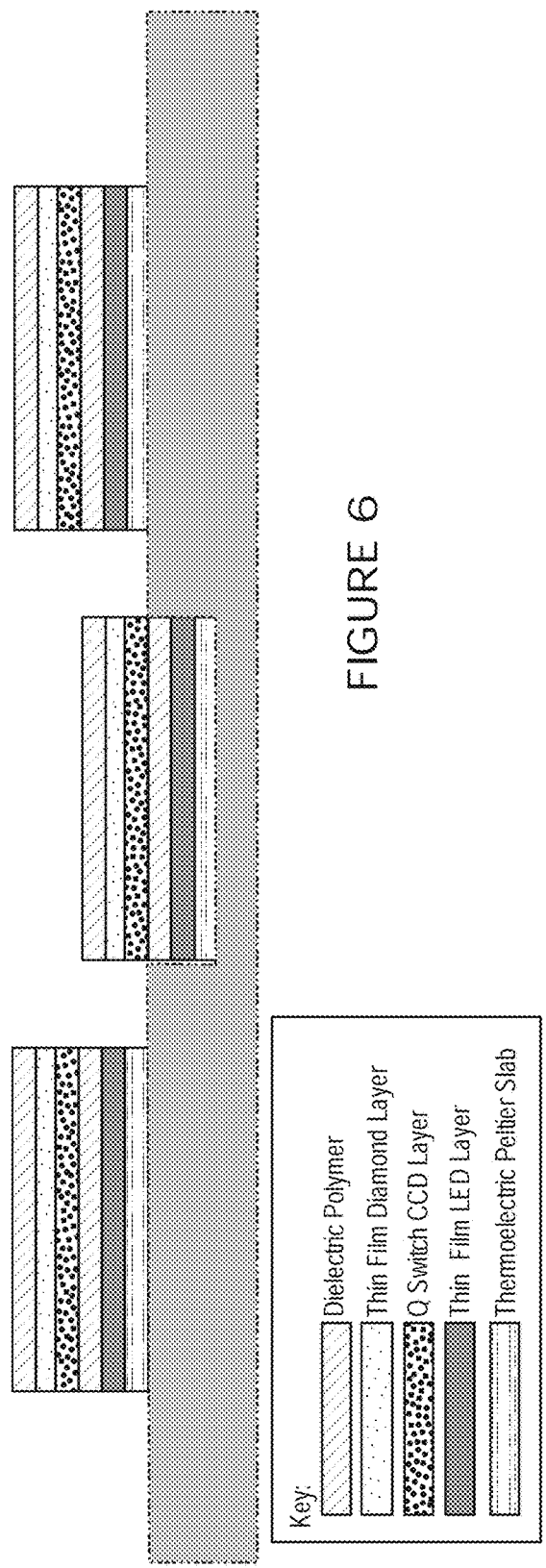
FIG. 6 is a schematic cross-sectional view of the thin panel, phased-emitter array shown in FIG. 5.

Referring to FIGS. 5 and 6, use of a phased array 28 of thin panel MASER emitters 10a, 10b is capable of generating MASER emissions that are stable and have long length coherence. A representation of a portion of a multi-element phased array 28 is shown in FIGS. 5 and 6. A plurality of emitters 10a, 10b are fabricated on or embedded in a thin panel substrate 30. Reference number 10a designates emitters fabricated on the surface of the thin panel substrate 30, and reference number 10b designates emitters embedded in the thin panel substrate 30, with a vertical spacing offset. The offset can be selected, e.g., to be compatible with a desired resolution of the interferogram if the phased array 28 is used in an imaging system as described in co-pending application Ser. Nos. 17/148,275, entitled "Phased-Array MASER Detector for Synthetic Aperture Interferometric Imaging," by James Joseph Cohen and Emad N. Eskandar, filed on even date herewith and incorporated by reference herein.

The assembly 28 is desirably manufactured using an epitaxial technology or similar means to generate an implantable, zero dangling-bond gain medium, that can be ion milled and implanted to achieve transitional vacancies at the desired Masing frequencies. Further, the stacked emitter 10a, 10b forms an addressable synthetic-aperture emitter, transparent to the optical pump except for the quantum lattice transition idealized by the ion implantation admixture.

In a typical MASER emitter or laser, the gain media is contiguous, and all the active moieties are essentially in one unit (such as a doped crystal) and potentially participate in the process of amplification. Coherent emission is achieved by stimulated emission through a population inversion. In essence, the gain media, composed of a great plurality of coupled re-radiative components are stimulated with a pump of energy. Thereafter, a preferred step of energy conversion is selected by stimulating the transition in a uniform manner. This causes a cascade of emission from the gain media in an energy signature and vector consistent with the overall resonation of the gain media. Other radiative transitions are minimized and occupy a fractional component of the energy conversion. The overall effect is that the light emission appears to be radiating from a single radiative element. The photon wave front is coherent and is synthesized from the overall emission topology.

A different approach is used to generate coherent emissions from the array 28 of discrete emitters 10a and 10b shown in FIGS. 5 and 6. As described above, Q-switching is a technique for disrupting transmission in a resonant cavity to allow for storage and emission of energetic pulses. In one embodiment of the invention, however, the goal is not to generate pulses but rather to drive continuous wave in-phase emissions from the individual emitters 10a, 10b. In this embodiment of the invention, the Q-switch layer 20 is mated to the active diamond layer 12, both of which are within the resonant cavity 14, 16 of each emitter 10. The Q-switch layer 20 is transparent to photons (in the visible range) pumped from the LED layer 18, but selectively scatters photons in the microwave range of interest. Depending on its state (low Q or high Q), the Q-switching layer 20 selectively interferes with microwave transmission, favoring coherent emission across the entire array 28, and dispersing the rest. It is this effect by which a quasi 2-dimensional emitter/gain media can produce a diffraction limited beam of consequence.

Provided that the wave propagating emitter 10 is stable and controllable, the Q-switch layer 20 is used to generate a coherent beam through the combined emissions of the individual emitters 10a, 10b. Before use, the thin panel array 28 of microwave emitters 10a, 10b is calibrated. Once the array 28 is powered and stable, the Q-switch layer 20 of each element 10a, is individually flipped from low-Q (non-permissive) to high-Q (permissive) to determine the time needed to reach the masing threshold. This is a stable quantity reflecting features peculiar of each element. Coherent emissions always start at the lowest point of the waveform.

Q-switching is achieved by putting a variable attenuator inside the microwave resonator cavity. When the attenuator is functioning, microwave radiation leaving the gain medium does not return, and masing cannot begin. This attenuation inside the cavity corresponds to a decrease in the Q factor or quality factor of the maser resonator. A high Q factor corresponds to low resonator losses per roundtrip, and vice versa. Initially, the gain medium is pumped with LED light energy (530 nm) while the Q-switch is set to prevent feedback of microwave radiation into the gain medium (producing a microwave resonator with low Q). This produces a population inversion, but MASER emission cannot yet occur since there is no feedback from the resonator. Since the rate of stimulated emission is dependent on the amount of light entering the gain medium, the amount of energy stored in the gain medium increases as the gain medium is pumped. Due to losses from spontaneous emission and other processes, after a certain time the stored energy will reach a maximum level; the medium is said to be gain saturated. At this point, the Q-switch device is quickly changed from low to high Q, allowing feedback and the process of microwave amplification by stimulated emission begins.

Once the timing of all the emitters 10a, 10b is ascertained, the Q-Switch layer 20 of each element 10 is programed with a small delay specific to that element. The slowest element has zero delay while faster elements have proportionately longer delays. Subsequently, coherent emission is initiated by first turning all the switches to low-Q (non-permissive). At the desired time, the individual emitters are flipped to high-Q (no disruption) with the programmed delays so that the faster elements begin emission at the same time as the slowest element. In this fashion, coherent emission from all the arrays starts at the same time. Since MASER emission always starts at the lowest point of the waveform, they are in-phase and the resultant beam, or wavefront, is coherent and mode-locked. Once masing begins, the Q-switches can be controlled to adjust phase and frequency of the beam, and can be controlled to include two or more characteristic frequencies, e.g. a coupling component and a modulation component of the beam.

Example—Nitrogen-Implanted, Epitaxial Diamond MASER. This example describes experiments showing that MASER emission is possible from a singular isotropic MASER emitter having an epitaxial layer as a gain medium. In this example, a 0.6μ film of single crystal, epitaxial diamond was formed atop a bare Luxeon™ Rebel LED operating at 530 nm. Reported operational parameters of the LED are listed in Table 2:

TABLE 2

| | |
|---|---|
| LED Color | 530 nm |
| Lumens @ 350 mA | 102 lm |
| Lumens @ 700 mA | 161 lm |
| Efficacy @ 350 mA | 100 Lm/W |
| Efficacy @ 700 mA | 68 Lm/W |
| Typical Wavelength (1) | 530 nm |
| Wavelength Range (1) | 520 to 540 nm |
| Beam Angle (2) | 125° |
| Rec. Operating Current | 700 mA |
| Max. Rated Drive Current | 1000 mA |
| Typical Forward Voltage | 2.9 Vf |
| Max. Forward Voltage | 3.51 Vf |
| Thermal Resistance | 16° C./W |
| Max Rec. Junction Temp | 150° C. |
| Operating Temperature | −40 to 135° C. |
| Overall Dimensions | 20 × 20 × 5 mm |
| Active LED | .2 mm × .2 mm × 60 μ |

The LED was supplied on a ceramic substrate and included conductive landing pads. The LED itself was supplied bare without an optical dielectric. The active LED had dimensions of about 0.2×0.2×0.060 mm (along with a thermal portion having a thickness of about 0.5 mm). The LED was prepared for chemical vapor deposition (CVD) of a Spin Hall spin-torque oscillator (STO) with microwave stimulated molecular beam epitaxy of a layer of cadmium telluride. The cadmium telluride is transparent at 530 nm and provided a smooth surface without defects over the area of major activity. Metrologic characterization of the CVD STO was done with an optical gonioreflectometer incremented in 200 nm steps.

A diamond epitaxial layer was formed by microwave stimulated molecular beam epitaxy through NdYag ablation of a richochet carbon target set at 90 degrees and about 1000 microns from the CVD STO layer. Ultra-high vacuum was maintained by an ion pump. In this manner, a diamond film of 635 nm was developed over a deposition time of about 175 seconds. Deposition was halted due to thermal limits of the substrate as measured by a solid-state temperature probe beneath the LED.

The diamond film was then ion implanted with free disassociated nitrogen at an energy of 64 KEV with a fluence of 1017 ions/sec/cm2. Implantation time was approximately 3 seconds. It was estimated that implantation efficiency was about 3%. A measurable and uniform color change was recorded.

Atop the diamond layer, a copper microstrip resonator was formed by lithographed CVD Cu. The microstrip geometry was controlled to achieve optimal resonance at 36.8 Ghz. This corresponds to the third resonant octave of the expected hyperfine transition sought in the Nitrogen center formed in the diamond layer.

The hetero-structure was powered by two lithium ion battery cells (3.4 V output) connected in parallel with a simple resistive load inserted to ensure a stable supply of voltage. The battery leads were soldered to the conductive landing pads on the ceramic substrate. The LED was observed to emit brightly upon powering on. The operating temperature of the system was between 29° C. and 43° C. after about an hour of operation.

MASER experimentation was temperature controlled by means of a large (30 gm) copper heatsink (i.e. thermal bonded to the ceramic substrate). Operation of the system was at 34° C. within 0.2° C. during the course of the testing. The testing period was about 10 minutes. The experiment was replicated several times.

MASER emission was recorded by a Gunn diode detector in a small tuned resonator mounted on a micro stage. The detector was incrementally moved by manual rotation of the thimble in increments of 2 microns. The resultant waveform resolved to be 3.7471 mm with a typical sinusoidal power decrement. Auxiliary noise was also present, but the main line predominated by at least one order of magnitude. The experiments showed that coherent single frequency MASER activity can be produced using nitrogen implanted, epitaxial crystal diamond.

In the exemplary MASER emitters depicted in FIGS. 4 through 6, the epitaxial crystal diamond should be made thicker than the 635 nm thickness in the experiments. Increased thickness renders the layer mechanically and thermally robust for implantation and use, and also increases efficiency. As discussed above, the thin film crystal diamond should be formed via epitaxial growth.

A more detailed description of the fabrication and use of epitaxial thin diamond film, secondarily implanted with nitrogen ions, as gain media for generating coherent microwave emissions, in the experiments is now described.

The only previously described method for generating continuous wave microwave emissions at room temperature relies on a bulk diamond crystal, doped with nitrogen. The use of such doped diamonds, crystals grown with nitrogen as an impurity, is impractical for commercial fabrication into flat panel arrays because it is difficult to control the density and uniformity of nitrogen doping to a sufficient degree. Moreover, the self-annealing aspects of bulk diamond crystals generally produces a plentitude of dangling bonds or rotated crystal nucleation centers. Such deformations result in an inelastic coupling sapping the efficiency of the elevation of electrons into a metastable transition inversion. Such an inversion is necessary for coherent emission ie. Masing. It is therefore understood that unannealed epitaxial material will elastically accommodate $Nv^{-1}$ vacancies and preferentially permit energy to be stored in a metastable state creating a significant population inversion.

In contrast to bulk material used in the prior art, the invention as mentioned is based on epitaxial thin diamond films secondarily implanted with nitrogen Ions. This technique can be recapitulated for large scale manufacturing by adapting existing processes, and generates gain media with highly favorable features, along with being of sufficient quality and uniformity, to be used in commercial applications.

Epitaxial Fabrication of Stress-Tolerant Thin Diamond Film. Diamond, along with its carbon-cousins graphite and graphene, is the best thermal conductor around room temperature, having thermal conductivity of more than 2,000 watts per meter per Kelvin, which is five times higher than the best metals such as copper.

The absorption coefficient of the color centers in the nitrogen implanted diamond filled at the pump wavelength is relatively high. Depending on the atomic percent in the implanted regime, absorption will range between 30 and 90 percent of the incident fluence. However, the conversion efficiency is low, averaging about 3%. The balance of this energy is converted through kinetic sinks into intense heat islands. Spreading the generated heat uniformly and removing it from the system is a vital process to ensure stable operation. Bulk material is best for thermally sinking active material under high stress. Yet, for the purposes described herein, the controlled gradient uniformity is critical as is the defect free lattice. These characteristics are not available in bulk material. The implantation depth in the hetero-epitaxial diamond film will hover about 2 microns. A thermal sink of 5 mass units is a nominal design goal. Further, implantation of nitrogen into otherwise single crystal zero dangling bond films sets up great stress. Unlike other materials, diamond is not readily annealable. Thin films close to the implantation depth will yield under the stress without creating dangling bonds. It is understood and accounted for that notwithstanding the toughness of diamond significant stress, both structurally and thermally induced, will result in instabilities and may cause potential catastrophic failure in the lattice structure.

Basic understanding of the fundamental processes in crystal growth as well as the structural quality of diamond synthesized by epitaxial deposition on iridium surfaces has reached a high level for samples with (001) orientation. Diamond deposition on the alternative (111) surface, as used in the preferred embodiment of the invention, is generally more challenging. Heteroepitaxy of diamond on Ir/YSZ/Si (111) with different off-axis angles and directions is the desired target. During the growth of the first microns, strong and complex intrinsic stress states were rapidly formed. They restricted the range of suitable temperatures in this study to values between 830° C. and 970° C. At low-stress conditions, the maximum growth rates were about 1µ/h. They facilitated long-time processes which yielded pronounced structural improvements with minimum values of 0.08° for the azimuthal mosaic spread, $4 \times 10^7$ cm−2 for the dislocation density and 1.8 cm−1 for the Raman line width. This refinement is even faster than on (001) growth surfaces. It indicates substantial differences between the two crystal directions in terms of merging of mosaic blocks and annihilation of dislocations. Crystals with a thickness of up to 330µ were grown but were not used for testing. The correlation of photoluminescence and µ-Raman tomograms with topography data also revealed fundamental differences in the off-axis growth between (001) and (111) orientation. The analysis of the microscopic structures at the growth surface provided the basis for explaining the intriguing reversal of stress tensor anisotropy caused by a simple inversion in sign of the off-axis angle.

Optimization of Nitrogen Doping for Coherent Emission. Nitrogen doping is used to achieve field emission from diamond, and hence it is important to be able to dope diamond with nitrogen in a controlled way, such as that offered by ion implantation. The procedure developed for optimizing p-type doping of diamond by B ion-implantation (cold implantation and in situ rapid annealing (CIRA) followed by high-temperature annealing) has been implemented here for N implantations. However, the preferred conditions would avoid the consequential annealing phase. Thereby building in stronger stressed structures and a refined energy coupling by Rabi processes. In the experiments performed, such annealing could not be avoided. Care was taken to minimize the annealing components. The implanted and annealed layer has been studied by EPR and by cathodoluminescence and photoluminescence measurements. These indicate that a high fraction of N can be incorporated into substitutional sites by the disclosed implantation procedure and that the so-treated N-implanted diamond much resembles N-containing type Ib diamond. In this manner, we achieved a gradient implantation of N into 111 oriented diamond film.

Local formation of nitrogen-vacancy centers in diamond by swift heavy ions. After nitrogen-implanting diamond films it was decided to expose the films to beams of swift heavy ions (~1 GeV, ~4 MeV/u) and find that these irradiations lead directly to the formation of nitrogen vacancy (NV) centers, without thermal annealing. Analysis required comparing the photoluminescence intensities of swift heavy ion activated $NV^-$ centers to those formed by irradiation with low-energy electrons and by thermal annealing. $NV^-$ yields from irradiations with swift heavy ions are 0.1 of yields from low energy electrons and 0.02 of yields from thermal annealing. Possible mechanisms of NV center formation by swift heavy ions such as electronic excitations and thermal spikes are expected. While forming NV centers with low efficiency, swift heavy ions could enable the formation of three-dimensional $NV^-$ assemblies over relatively large distances of tens of micrometers. Results show that NV center formation is a local probe of (partial) lattice damage relaxation induced by electronic excitations from swift heavy ions in diamond.

The following description is directed to the mechanism of formation of $NV^-$ centers, why these centers are essential for the masing action and how SHI and low energy electron (e-) irradiation lead to the production and activation of $NV^-$ centers. The primary goal in this experiment was to raise the conversion efficiency for stable masing. In diamonds that were doped with nitrogen during the growth process NV centers can be formed by creating vacancies using irradiations with energetic photons, neutrons, electrons or ions followed by thermal annealing above 600□0C. It was observed that vacancies become mobile and substitutional nitrogen atoms (Ns or P1 centers) can capture single vacancies, forming NV centers. In pure diamonds, nitrogen can be added by implantation of nitrogen ions. Ion implantation offers control over the local nitrogen and NV center concentrations with high spatial resolution. When implanting a diamond with nitrogen ions, e.g. of keV to MeV energies, ions transfer kinetic energy to carbon atoms in elastic collisions, leading to collision cascades that generate vacancies and carbon interstitials. Implanted nitrogen ions come to rest mostly on interstitial lattice sites, though replacement collisions are also possible. The formation of NV centers in nitrogen implanted diamond has been assumed to follow a two-step process. During annealing above 600° C., implanted nitrogen atoms can first be incorporated on substitutional lattice sites, forming P1 centers. Vacancies can diffuse through the diamond lattice during thermal annealing and the second step in NV formation is the trapping of a vacancy at the site of a substitutional nitrogen atom. The charge state of the resulting NV centers is affected by the local nitrogen concentration, the defect environment and by surface conditions. Only $NV^0$ and $NV^-$ centers are observed in photoluminescence (PL) or cathodoluminescence (CL) measurements. Reported efficiencies for the conversion of implanted nitrogen atoms to NV centers depend on the nitrogen implant energy and processing conditions (including implantation with elevated target temperatures) and range from below 1% to about 25% for low energy nitrogen implants (<100 keV).

Hydrogen, present from growth or introduced into diamonds during annealing can interact with NV centers and quench their photoluminescence. Care was taken to avoid hydrogen contamination. However, the star-ion pump saturation threshold was reached quickly and the resultant pollution of the lattice by incorporated hydrogen impurities was unavoidable. The atomic percent was quite small on the order of 0.01 log atomic percent and was ignored as insubstantial.

Recent simulations of NV center formation in diamonds with high concentrations of substitutional nitrogen suggest that NV centers form during exposure to vacancy-producing irradiation and not during thermal annealing. The reason for this is the apparently higher likelihood for di-vacancy vs. NV formation during annealing.

NV centers also form in nitrogen-implanted, electronic grade diamond during exposure to low-energy electrons (1-30 keV) without any thermal annealing. This result showed that the commonly accepted two-step model of NV formation in electronic grade, nitrogen-implanted diamond is incomplete.

Electronic excitations induced by swift heavy ions (SHI) also lead to the local formation of NV centers without thermal annealing. SHI such as gold or uranium ions with kinetic energies of ~1 GeV, near the Bragg peak in electronic energy loss, deposit kinetic energy mostly through inelastic collisions with target electrons at a rate of about 50 keV/nm in diamond. Energetic electrons quickly thermalize in cascades, forming many thousands of electron-hole pairs per SHI. Lattice heating through electron phonon coupling and from bond reorientation can lead to thermal spikes effects in the material surrounding the ion trajectory. Relative yields of $NV^-$ centers formed by SHI were compared to exposure to low energy electrons and compared to thermal annealing and alternative possible mechanisms of $NV^-$ formation by SHI were also noted. Insights into the interplay of electronic excitations and thermal annealing might lead to improved processing strategies for reliable formation of $NV^-$ centers with high placement resolution, spectral stability, and favorable spin properties.

An experiment was performed to determine the result of nitrogen implantation and SHI and electron radiation. After cleaning in a mix of sulfuric, nitric and perchloric acid (1:1:1) two electronic grade diamond samples (<5 ppb nitrogen content, size of 4 $mm^2 \times 1\mu$ thick were implanted with $^{14}N^+$ ions. The implant spots were 1 mm in diameter, and we aligned them so that they did not overlap. Each diamond was implanted with 10 and 30 keV nitrogen ions and for both implant energies two fluences, $10^{12}$ and $10^{13}$ N $cm^{-2}$ were applied for a total of four implant spots on each diamond. The implantation depths for these implant conditions were less than 130 nm, including channeling tails. Irradiations with SHI were performed at the GSI Helmholtz Center using 1.14-GeV U ions of fluence $5 \times 10^{11}$ $cm^{-2}$ and 1.16-GeV Au ions ($10^{11}$ $cm^{-2}$). The projected range of these ions in diamond is in excess of the full thickness of the film and extended about 30µ into the substrate, far beyond the 100 nm thick nitrogen-implanted layer. The higher fluence, uranium—implanted sample showed a visible greenish discoloration presumably from vacancy related color centers, such as GR1 centers, formed by displacement damage preferentially at the end of the ion range. The focus of this work was on $NV^-$ and did not track details of GR1 center formation and annealing.

During SHI irradiations the samples were masked with a honeycomb patterned metal grid with a thickness much larger than the range of the SHI. Analysis was concentrated on results from the uranium irradiated sample because signal levels from the sample irradiated with the lower fluence of gold ions were low.

Figure 7:
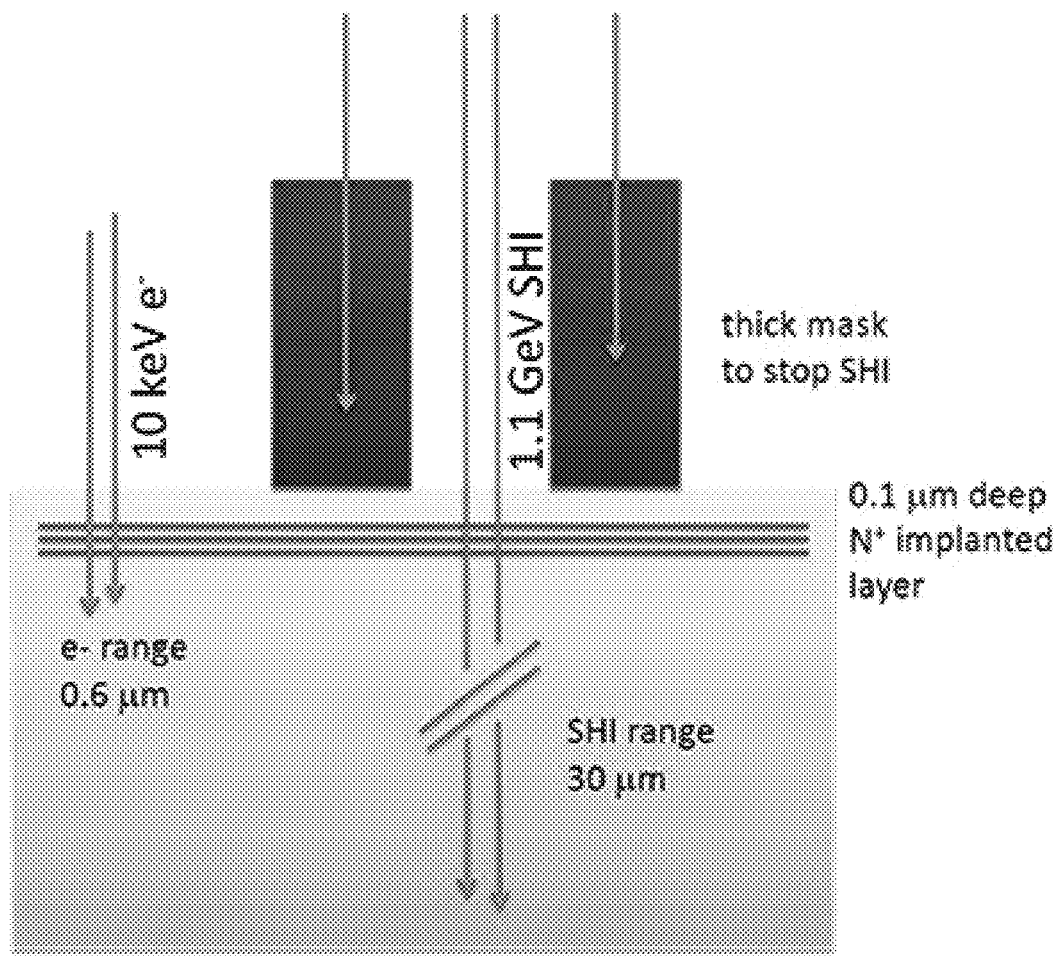
FIG. 7 is a schematic diagram illustrating irradiation conditions of nitrogen-implanted epitaxial diamond by swift heavy ion (SHI) radiation and low-energy electron radiation.

In order to compare results from SHI irradiation to our previous results from low-energy electron bombardment, three different sample areas (pristine diamond, nitrogen implanted, nitrogen implanted and SHI irradiated) were exposed to a high fluence of 10 keV electrons in a scanning electron microscope (SEM). The applied electron fluence was 90 C/cm$^2$ corresponding to saturation of the observed NV$^-$ yield reported earlier for diamonds that had been implanted with the same fluences of nitrogen ions. A schematic of the implant conditions is illustrated in FIG. 7. The masked SHI irradiations resulted in sharp contrast in hyperspectral imaging between the neighboring irradiated and masked regions as seen in FIG. 8.

For optical characterization hyperspectral imaging at room temperature using a grating spectrometer Raman Microscope with 0.8 NA air objective and a laser of wavelength 532 nm was used. All different exposure combinations were analyzed and compared by integrating the peak area around the NV$^-$ zero-phonon line (ZPL) before and after annealing at 850° C. FIG. 8 shows a hyperspectral image obtained by integration over the wavelength range of 635-642 nm around the ZPL of the NV$^-$ centers. The large circular zone (lighter shade, indicated by the white line) corresponds to the spot of the nitrogen implantation. Regions covered with the honeycomb shaped metal mask during SHI irradiation appear as dark lines. The dark area (1) outside the nitrogen implant spot thus corresponds to pristine diamond that was neither implanted with nitrogen nor exposed to SHI. Area (2) outside the implantation spot was exposed only to 1.14 GeV uranium ions ($5\times10^{11}$ cm−2) and shows a PL signal from single vacancies (GR1 center) caused by lattice displacements from the SHI impacts, but no NV$^-$ signal. Region (3) was implanted with nitrogen as well as exposed to SHI and shows NV$^-$ centers with a relatively low intensity. Areas that were implanted with nitrogen but then masked from SHI impacts (4) show NV$^-$ only after irradiation with low-energy electrons. We also irradiated N-implanted and SHI-irradiated areas in micron scale spots with a 10-keV electron beam (5) to explore possible additive effects in NV formation from consecutive SHI and electron exposures.

Figure 8:
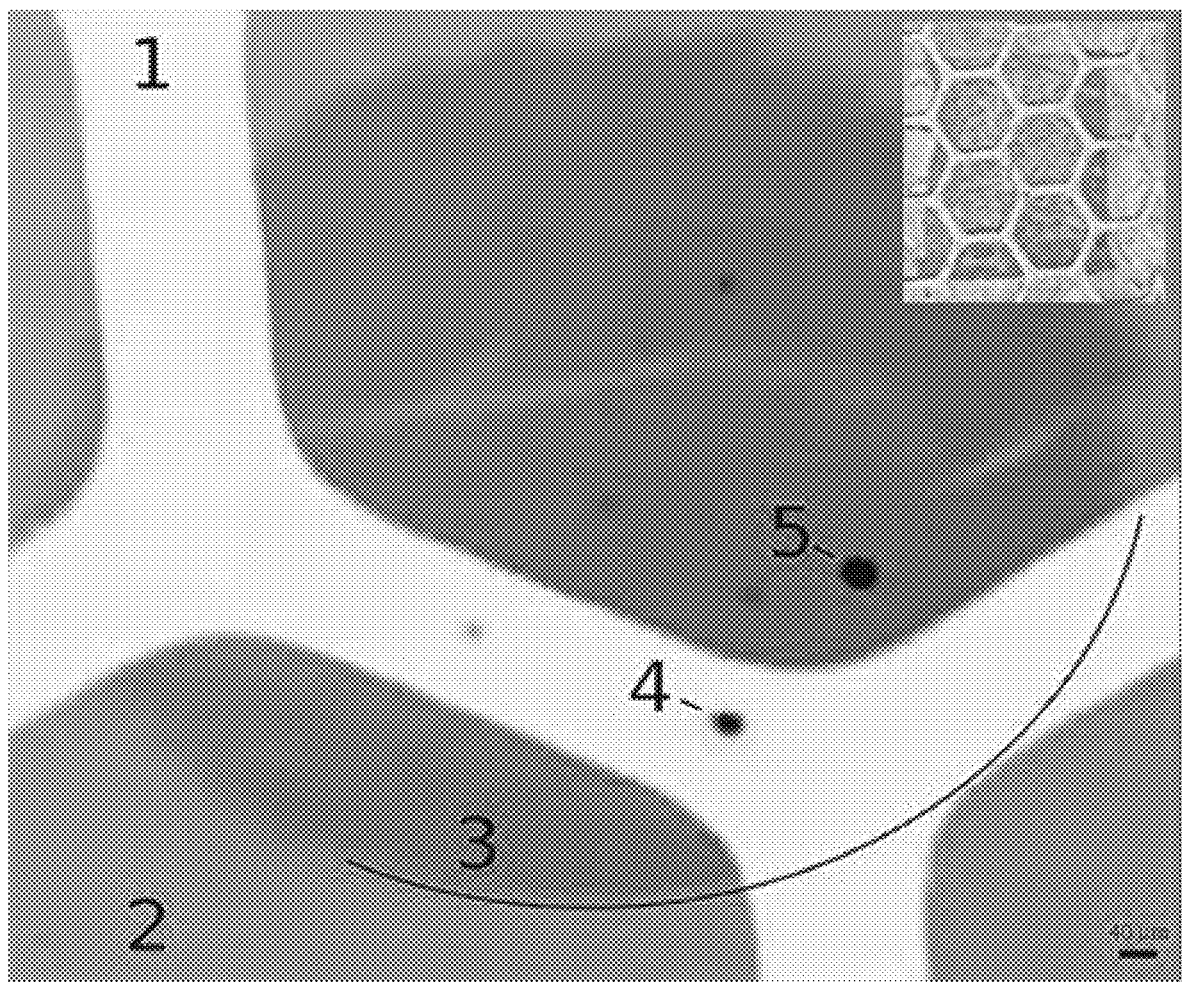
FIG. 8 is a hyperspectral image of photoluminescence (PL) intensity from $NV^-$ centers (635-642 nm) in epitaxial diamond under various experimental conditions of irradiation.

Photoluminescence (PL) spectra for each of the six different areas in FIG. 8 before (FIG. 9) as well as after thermal annealing at 850° C. for 1 h (FIG. 10) was collected.

The intensity of NV$^-$ ZPL signals from exposure to SHI was relatively low. The NV$^-$ ZPL signal also overlaps with the tail of the GR1 center signal and this led to uncertainty in the assessment of the relative NV$^-$ formation efficiency from SHI. For background correction in N-implanted regions that were masked from SHI exposures (4), we used data from pristine diamond areas (1), which were found to be spectrally equivalent to N-implanted areas prior to thermal annealing. With a given sensitivity and signal to noise, there was no observed NV$^-$ centers in pristine diamond areas or nitrogen implanted areas that had not been exposed to either SHI or electrons prior to thermal annealing.

Figure 11:
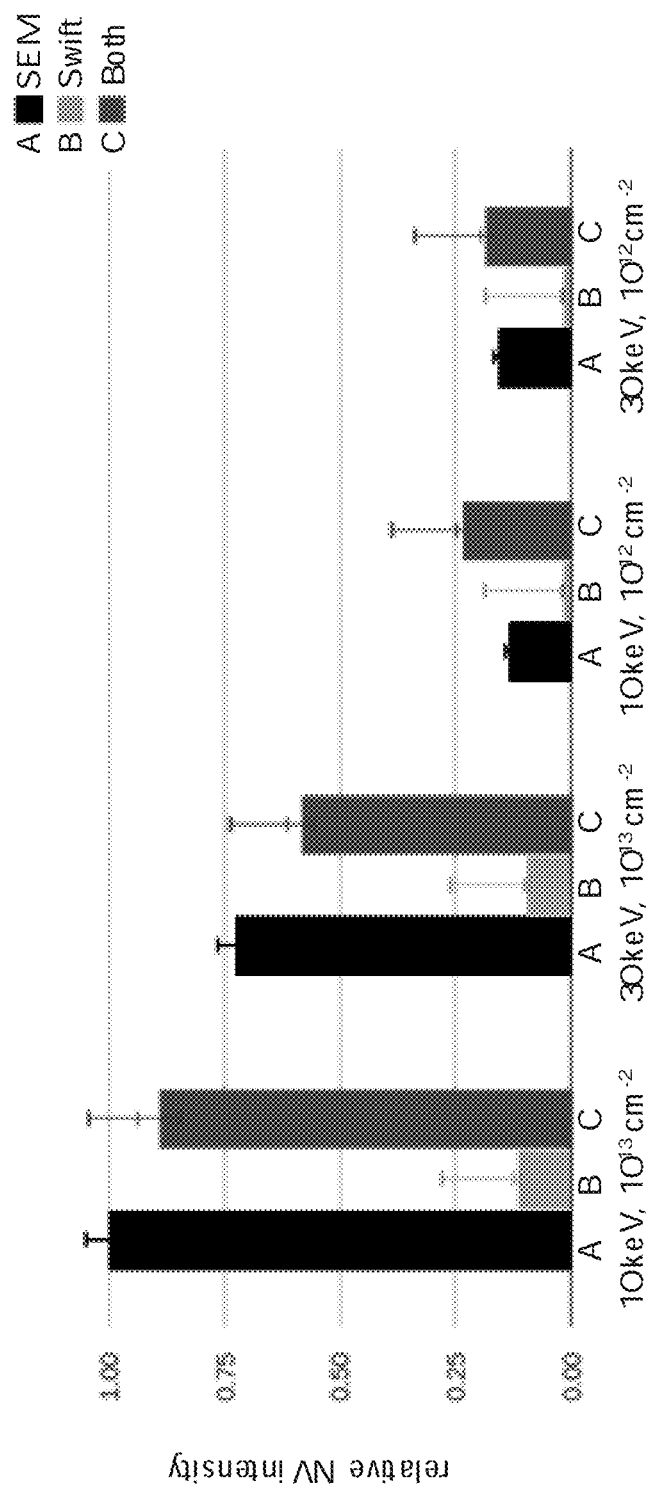
FIG. 11 is a plot illustrating relative $NV^-$ PL intensities from exposure to SHI and to low energy electrons for a series of N+ implantation energies and fluences without thermal annealing. For SHI alone and both treatments, the damage signal from SHI irradiation of pristine diamond areas was subtracted. The PL intensity before background subtraction is indicated by the top of the error bars. For the electron treatment, the background signal measured from pristine diamond was subtracted. The data is normalized to an $NV^-$ signal from a $10^{13}$/cm2 10 keV N+ implant followed by exposure to 10 keV electrons.

The passage of SHI through nitrogen implanted layers in diamond leads to the formation of NV$^-$ centers (FIG. 9, N and SHI) without thermal annealing. The yield of NV$^-$ centers formed directly by a fluence of $5\times10^{11}$ U-ions/cm$^2$ (1.14 GeV) is about 0.1 of yields from exposure of nitrogen implanted diamonds to 10 keV energy electrons (90 C/cm$^2$) and about 0.02 of NV$^-$ yields from thermal annealing. The highest NV$^-$ intensities when nitrogen implanted areas were first exposed to SHI and then also to low energy electrons (FIG. 8, N, SHI and electrons). But this spectrum includes a contribution from the tail of the GR1 center line and after subtracting it from the NV$^-$ ZPL area, the NV$^-$ yields from electron exposures and electron plus SHI are about equal (FIG. 11).

After thermal annealing, the NV$^-$ signal is higher in areas that had been irradiated with either SHI or keV electrons compared to areas that had been implanted with nitrogen but not irradiated further. Combining both irradiations and thermal annealing produces the highest NV$^-$ yields (FIG. 8, N plus SHI plus electron, and FIG. 11), higher than thermal annealing alone.

Figure 1:
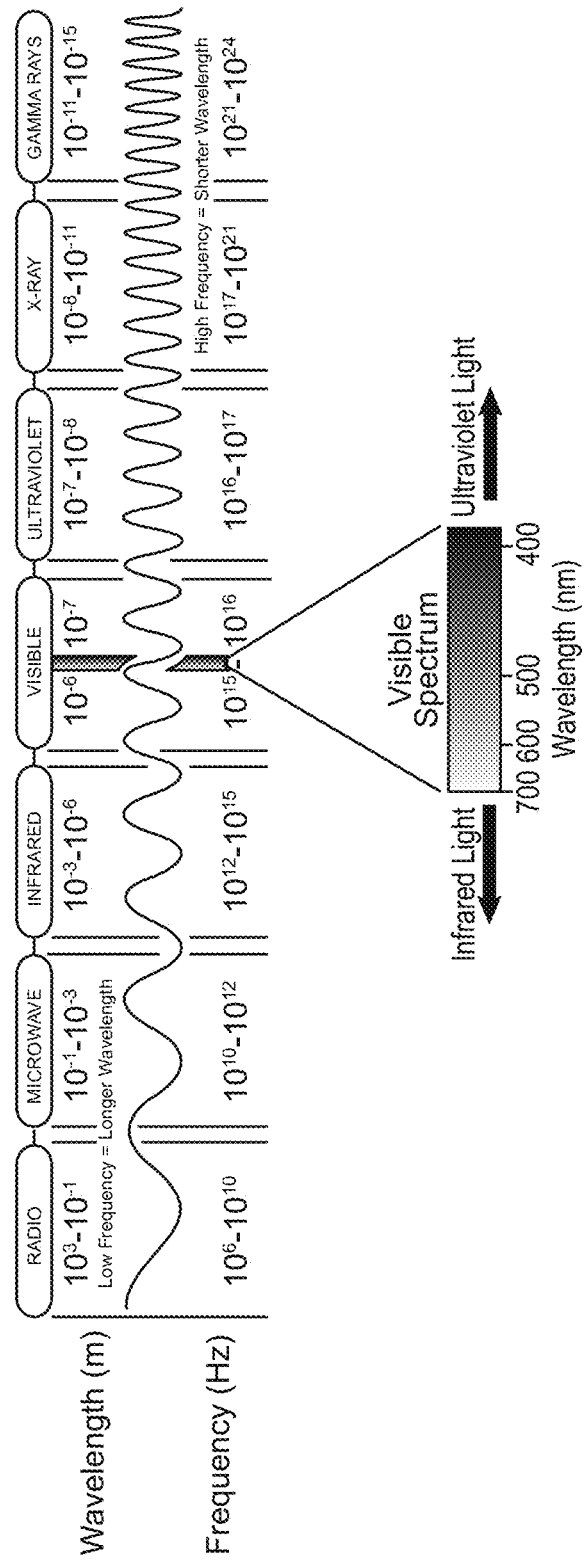
FIG. 1 is a diagram illustrating wavelength and frequency along the electromagnetic spectrum.
Figure 2A:
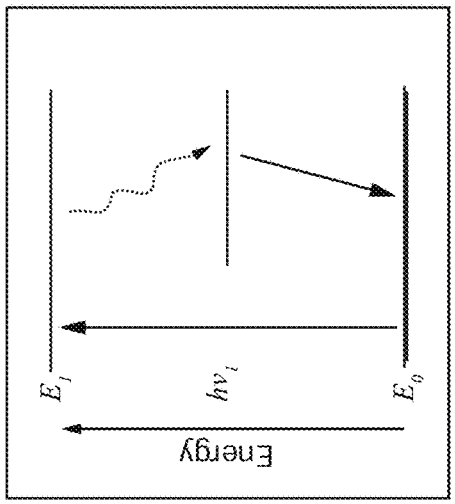
FIGS. 2A and 2B are Jablonski diagrams illustrating the relaxation of a molecule or atom to a lower energy state through emission of photons (FIG. 2A) and relaxation of a molecule or atom to a lower energy state through loss of heat and photon emission (FIG. 2B).
Figure 2B:
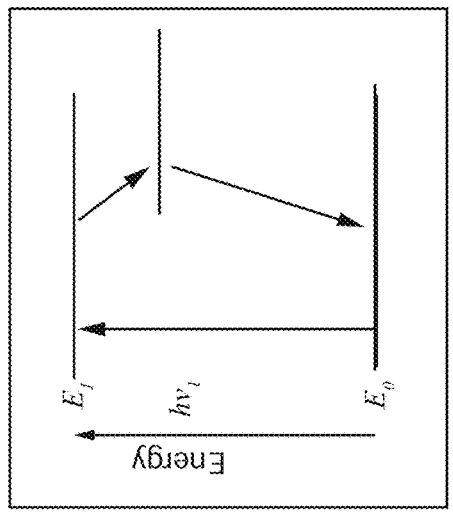
Figure 3:
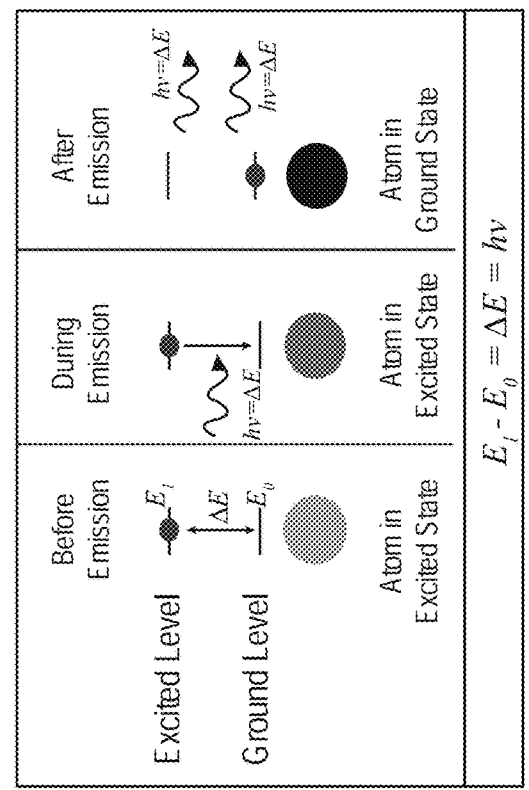
FIG. 3 is a diagram illustrating stimulated emission.
Figure 9:
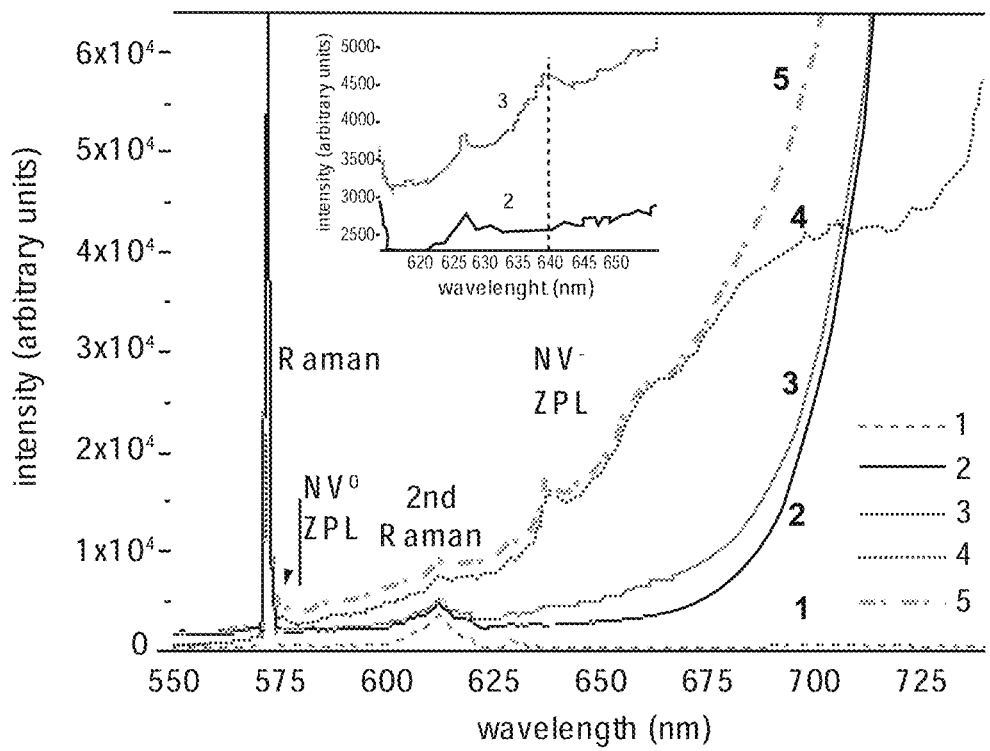
FIG. 9 is a plot depicting PL intensity under the various experimental conditions illustrated in FIG. 8, before thermal annealing. The inset is a plot of Raman intensity for experimental conditions 2 and 3 in FIG. 8.
Figure 10:
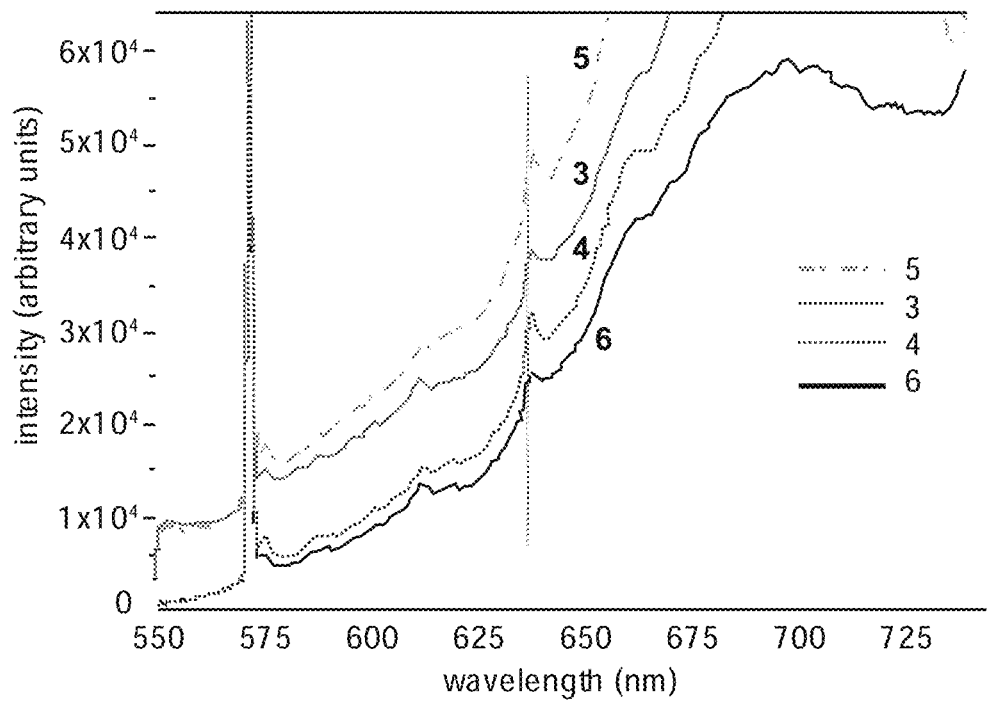
FIG. 10 is a plot depicting PL intensity under the various experimental conditions illustrated in FIG. 8, after thermal annealing.

To compare the PL intensities more quantitatively the SHI induced GR1-center contribution were subtracted from the NV$^-$ ZPL area (635-642 nm) and normalized all measurements to PL signals from 10 keV N-implants ($10^{13}$ cm$^{-2}$) followed by exposure to 10 keV electrons (>90 C/cm$^2$). These data were extracted from spectra similar to those in FIG. 3. The N to NV$^-$ conversion efficiency from electronic activation using low energy electrons is ~25% of that from standard thermal annealing (850° C., 1 h). Thermal annealing itself has a formation efficiency for NV$^-$ centers from −10 keV nitrogen implants of only a few percent. The formation of NV$^-$ centers by SHI (U ions, 1.14 GeV, $5\times10^{11}$ cm$^{-2}$) yields approximately 10% of the PL intensity of a 10 keV e-beam (90 C/cm$^2$). The estimate for the absolute conversion efficiency from implanted nitrogen to NV$^-$ centers, NV$^-$/N, from the uranium ion irradiations is $5\times10^4$ to $10^{-3}$. In FIG. 11 relative NV$^-$ yields before global annealing, from spectra as in FIGS. 9 and 10, are compared. The data in FIG. 11 was recorded before thermal annealing and were normalized to the reference implant ($10^{13}$/cm$^2$, 10 keV N$^+$) that had also been irradiated with a saturation dose of low energy electrons. The top of the error bar indicates the yields from raw data before subtraction of contributions from GR1 centers to the NV$^-$ ZPL. Within the uncertainty of background subtraction, exposing a nitrogen-implanted diamond first to $5\times10^{11}$ U-ions/cm$^2$ and then to low energy electrons does not yield significantly more NV$^-$ centers compared to the exposure to low energy electrons alone for the sample implanted with a fluence of $10^{13}$ N/cm$^2$. Trends are similar for the 10 keV and 30 keV nitrogen implants and for the sample implanted with $10^{12}$ N/cm$^2$. However, the latter uncertainties are increased due to lower signal levels and background contributions from GR1 centers.

The formation of NV$^-$ centers by means of low-energy electron exposure does not exhibit a threshold in electron beam energy and does not depend on the e-beam current density, indicating that the formation process is not dominated by momentum transfer or target heating but rather by electronic excitations induced by the electron beam. Deposition of kinetic energy of SHI along their trajectory in diamond is also dominated by electronic excitations with an electronic stopping power of ~50 keV/nm and only a small contribution from elastic collision processes (<0.1 keV/nm and ~0.25 vacancies) in the ~130 nm deep nitrogen—implanted layer. Collisions of 1.14 GeV U-ions with target electrons can produce electrons with up to −10 keV of kinetic energy. Subsequent electron-electron collisions lead to a cascade with a distribution of low-energy electrons. The cascade electrons thermalize within a few picoseconds, followed by radiative and non-radiative recombination or charge trapping at defect sites. The kinetics and relaxation mechanisms of the electron cascade are similar to those occurring during irradiation with keV electrons, though details of the energy, depth, and lateral distributions differ greatly. The main difference is the high excitation density of SHI with electronic energy loss rates of tens of keV/nm that can induce local thermal spike effects including localized melting and rapid re-crystallization. Whether SHI form NV centers directly via electronic excitations similar to processes during irradiation with keV electrons, or if thermal spike effects play a role is an unknown. In thermal spikes, the high electronic energy loss of projectiles can induce local melting of materials along the ion trajectory.

In diamond, no permanent tracks have been observed, indicating that re-crystallization leads to at least partial lattice reconstruction following passage of SHI. The observation of $NV^-$ centers does indicate partial lattice reconstruction of the nitrogen implanted layer in diamond following passage of SHI, while the presence of substitutional nitrogen atoms (P1 centers) is a measure of more complete damage repair. $NV^-$ can be detected by optical microscopy while the analysis of P1 centers and other non-luminescent defect complexes can be probed e.g. via spin resonance, dark state spectroscopy or structural probes such as transmission electron microscopy.

In order to elucidate possible mechanisms of $NV^-$ formation by SHI consider the qualitatively electronic excitation processes from SHI and exposure to low energy electrons. For low energy electrons we found an increase of the $NV^-$ intensity with increasing electron exposure up to a saturation fluence of □10 C/cm². If one considers the electronic stopping of 50 keV/nm for 1.14 GeV U-ions, a fluence of $5 \times 10^{11}$ cm⁻² and an energy for the formation of an electron-hole pair in diamond of 13 eV, then it can be estimated that the SHI irradiation generates of the order of $2 \times 10^{17}$ electron-hole pairs/cm² in the 100 nm wide nitrogen implanted layer. For comparison to earlier measurements of the fluence dependent $NV^-$ formation from low energy electrons, the equivalent low electron fluence from SHI is then about 30 mC/cm². For low energy electrons, this fluence would corresponded to a relative $NV^-$ intensity of 500 from a 100 nm thick, nitrogen implanted layer, about 4 times lower than a relative intensity of 2000 for a saturation fluence (>10 C/cm²) of low energy electrons. The experiment demonstrates $NV^-$ are formed by SHI with a relative intensity ten times lower compared to the $NV^-$ center intensity from a high fluence of low energy electrons. Within this very rough estimate, SHI appear to be 2.5× less efficient in forming $NV^-$ centers than electrons per keV of electronic energy loss in the nitrogen implanted layer.

Thermal spike effects could also play a role in $NV^-$ formation by SHI. SHI can induce thermal spikes by their high density of electronic energy deposition. Along the projectile trajectory, a hot cylindrical zone is created with a heating and cooling time of a few ps. It is predicted that temperatures well above the (pressure dependent) stability limit of $NV^-$ centers of about 1200 to 2000° C. can be reached within the cylinder core of ~5 nm radius. This hot core is surrounded by progressively cooler regions. Within an area of about 200 nm² the temperature can still be above 600° C. and induce vacancy mobility for a brief period. It seems plausible that SHI can stimulate $NV^-$ formation in a region surrounding the ion trajectory that is heated, but not to a temperature above the NV stability limit. Here, $NV^-$ centers can form by the two-step process of nitrogen incorporation into the lattice followed by capture of a mobile vacancy, and by a combination of electronic excitation and thermal activation for reconstruction of defect complexes that contain interstitial nitrogen and vacancies. At the given fluence for U ions of $5 \times 10^{11}$ cm⁻² and an estimated heated area per ion of ~200 nm², all nitrogen ions (implanted with a with fluence of $10^{13}$ cm⁻²) experience both a local thermal transient together with electronic excitations.

Following SHI irradiation and keV-electron exposures, a standard thermal annealing process was applied. After annealing, the $NV^-$ yields are higher in areas that were exposed to electrons or first exposed to SHI and then to electrons, compared to thermal annealing alone. SHI irradiations form NV's directly, but with relatively low efficiency. Apparently, SHI irradiation also modifies the structure of the nitrogen implanted layer such that consecutive exposure to keV electrons produces slightly more NV centers than electron exposure alone, without SHI pre-treatment. For the 10 keV nitrogen implant with fluence of $10^{13}$ cm⁻², it is found that the combination of SHI, followed by electron beam and finally thermal annealing produces the highest $NV^-$ yields, more than thermal annealing alone, and more than electron exposure plus thermal annealing. For the 30 keV nitrogen implant, $NV^-$ formation by 10 keV electrons is less efficient, probably because electrons lose more energy before reaching the peak of the implanted nitrogen distribution. Trends are similar for nitrogen implants with $10^{12}$ cm⁻² but signal levels were lower.

Both low energy electrons and SHI can also affect defect complexes of NV centers with hydrogen. No characterization of the hydrogen content of the diamonds used here. This is likely a small effect present where hydrogen related $NV^-$ PL quenching effects were observed following specific hydrogen plasma treatments.

Simple steps enable the formation of three-dimensional $NV^-$-N assemblies by means of SHI irradiation. First, electronic grade diamond is implanted with a selected depth profile of nitrogen ions, e.g. using multiple implantation energies. In a second step, the diamond is irradiated with SHI and $NV^-$ centers are formed along the ion trajectories. Assemblies of $NV^-$ can be tailored with a distribution of $NV^-$ spacings resulting from the local nitrogen concentrations and N to $NV^-$ conversion efficiencies.

Local $NV^-$ formation without global thermal annealing also enables a try-and-repeat approach to $NV^-$ array formation. After a single nitrogen ion is implanted and registered in a selected location, an $NV^-$ center can be formed by low energy electron irradiation, by targeted SHI irradiation or by another form of local excitation. The location can be repeatedly probed for the presence of an $NV^-$ center by PL or CL. Once an $NV^-$ is detected, the process is repeated at the next location or more nitrogen and vacancies can be introduced by local ion implantation, followed by local excitation until an NV-center is observed. In this way, arrays of single NV centers can be formed. Coherence times of locally formed $NV^-$ have to be quantified to evaluate their potential uses.

$NV^-$ yields from exposure of nitrogen implanted diamonds to SHI and keV electrons followed by a standard thermal annealing step are ~1.7× higher than yields from thermal annealing alone. But absolute conversion yields, $NV^-$/N, are still low, of order a few percent. Results show that the simple model of $NV^-$ formation in nitrogen implanted diamond in a two-step process of P1 center formation followed by vacancy trapping at substitutional nitrogen sites is incomplete. SHI can form $NV^-$ centers along tracks like "pearls on a string" over distances of tens of µm's. Local $NV^-$ formation by SHI or low-energy electrons enables try-and-repeat approaches for the deterministic formation of NV center arrays in which nitrogen is first implanted and then locally activated. Further, findings support the confirmation of predictions that NV formation by the passage of SHI in pre-implanted and pre-damaged diamond shows that NV⁻ centers are probes of (partial) lattice damage recovery. Tracking of NV⁻ centers and other color centers may be useful in studies of lattice damage and recovery dynamics in the interplay of elastic and inelastic energy loss process during irradiations.

NV⁻ lattice defects for use in continuous wave MASER films is achievable in unannealed systems provided thermal runaway is controlled and preferential annealing is prevented. The conversion of NV to NV⁻ lattice vacancies is a critical threshold which must be observed. Localized bond shifts will occur at energies far below bulk annealing temperatures. Such shifts will prevent metastable inversion and broaden the hyperfine transitions. In such a case, masing efficiency will be greatly reduced and may prevent a population inversion.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

What is claimed is:

1. A MASER emitter capable of outputting coherent microwave energy, comprising:
    a first dielectric polymer resonator layer;
    a second dielectric polymer resonator layer;
    a gain medium comprising a thin film epitaxial layer of nitrogen-implanted crystal diamond,
    a Q-switch CCD controlled layer of nematic molecules located adjacent the gain medium, wherein the gain medium and the Q-switch are located between the first and second dielectric polymer resonator layers, said Q-switch being controllable between a high Q factor setting and a low Q factor setting;
    an LED layer that outputs light that passes through at least the first dielectric polymer resonator layer to pump photons into the gain medium at a level sufficient to cause coherent microwave emission from the gain medium in continuous wave mode when the Q-switch is set to the high Q factor setting.

2. The MASER emitter recited in claim 1 further comprising a thermo-electric Peltier slab layer oriented adjacent the LED layer.

3. The MASER emitter recited in claim 2 wherein the thermo-electric Peltier slab layer is formed on an underlying substrate, the LED layer is formed on the thermo-electric Peltier slab layer, the first dielectric polymer resonator layer is formed on the LED layer, the Q-switch CCD controlled layer of nematic molecules is formed on the first dielectric polymer resonator layer, the thin film epitaxial layer of nitrogen-implanted crystal diamond is formed on the Q-switch CCD controlled layer of nematic molecules, and the second dielectric polymer resonator layer is formed on the thin film epitaxial layer of nitrogen-implanted crystal diamond.

4. A phased array comprising a plurality of MASER emitters as recited in claim 1, each arranged in a two-dimensional array and each capable of emitting continuous wave, coherent microwave radiation, wherein the respective Q-switch layers are controlled to appropriately delay MASER emission from the respective MASER emitters in order to form a combined emission from the plurality of MASER emitters in the phased array that is a single mode-locked, beam of coherent, continuous wave MASER radiation.

5. The phased array comprising a plurality of MASER emitters recited in claim 4 wherein a first group of emitters are located in a first plane, and a second group of emitters are located in a second parallel plane and offset spatially from the first plane.

6. The phased array comprising a plurality of MASER emitters recited in claim 4 wherein the emitters are arranged in column and rows.

7. The phased array comprising a plurality of MASER emitters recited in claim 4 wherein the emitters are arranged in a circular pattern or a star pattern.

8. The phased array comprising a plurality of MASER emitters recited in claim 4 wherein the distribution of energy in the coherent, mode-locked continuous wave MASER radiation is orthogonally Gaussian.

9. The phased array comprising a plurality of MASER emitters recited in claim 8 wherein Gaussian orthogonality is achieved by adjusting the LED pump energy and coordinating the operation of the Q-switches.

10. The phased array comprising a plurality of MASER emitters recited in claim 4 wherein the thickness of the epitaxial gain medium is no less than 5 micron and no more than 40 microns.

11. The MASER apparatus recited in claim 4 wherein the Q-switches are controlled to adjust phase and frequency of the beam such that the beam includes a first characteristic frequency for a coupling component of the beam and a second characteristic frequency for a modulation component of the beam.

12. A MASER apparatus capable of outputting continuous wave, coherent microwave radiation, comprising:
    a gain medium comprising a layer of nitrogen-implanted, epitaxial diamond;
    a first resonator layer located on a first side of the layer of nitrogen-implanted, epitaxial diamond;
    a second resonator layer located on a second side of the layer of nitrogen-implanted, epitaxial diamond; and
    an LED that outputs light to pump photons into the gain medium at a level sufficient to cause continuous wave, coherent microwave emission.

13. The MASER apparatus recited in claim 12 wherein the layer of nitrogen-implanted, epitaxial diamond has a thickness of no greater than 40 microns.

14. The MASER apparatus recited in claim 13 wherein the nitrogen-implanted, epitaxial diamond has a thickness of no greater than 30 microns.

15. The MASER apparatus recited in claim 12 wherein the first resonator layer is a Spin Hall, spin torque oscillator.

16. The MASER apparatus recited in claim 12 wherein the second resonator is a lithographed chemical vapor deposited copper layer.

17. The MASER apparatus recited in claim 12 further comprising a heat sink thermally connected to the LED.

18. The MASER apparatus recited in claim 12 wherein the MASER apparatus operates between 29° C. and 43° C.

19. The MASER apparatus recited in claim 12 wherein the layer of nitrogen-implanted, epitaxial diamond is exposed to radiation by a beam of swift heavy ions during the fabrication process.

20. The MASER apparatus recited in claim 19 wherein the layer of nitrogen-implanted, epitaxial diamond is also exposed to radiation by a beam of low energy electrons during the fabrication process.

* * * * *